(12) United States Patent
Picha et al.

(10) Patent No.: US 11,278,427 B2
(45) Date of Patent: Mar. 22, 2022

(54) SPINAL INTERBODY CAGE COMPRISING TOP AND BOTTOM FACES WITH MESH STRUCTURES, PILLARS AND SLOTS

(71) Applicant: GARY A. ZWICK, TRUSTEE OF THE EVEREST TRUST UTA APRIL 20, 2017, Cleveland, OH (US)

(72) Inventors: George J. Picha, Brecksville, OH (US); Grant Wesley Phillips, Richfield, OH (US); Rachel Smith, Brecksville, OH (US); James Price, Stow, OH (US); Gregory Causey, Erie, CO (US)

(73) Assignee: GARY A. ZICK, TRUSTEE OF THE EVEREST TRUST UTA APRIL 20, 2017, Cleveland, OH (US)

( * ) Notice: Subject to any disclaimer, the term of this patent is extended or adjusted under 35 U.S.C. 154(b) by 45 days.

(21) Appl. No.: 17/046,358

(22) PCT Filed: Apr. 9, 2019

(86) PCT No.: PCT/US2019/026613
§ 371 (c)(1),
(2) Date: Oct. 9, 2020

(87) PCT Pub. No.: WO2019/199850
PCT Pub. Date: Oct. 17, 2019

(65) Prior Publication Data
US 2021/0154023 A1    May 27, 2021

Related U.S. Application Data

(60) Provisional application No. 62/655,418, filed on Apr. 10, 2018.

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2/442* (2013.01);
(Continued)

(58) Field of Classification Search
CPC .......... A61F 2/44; A61F 2/442; A61F 2/4455; A61F 2/446; A61F 2/4465; A61F 2/447;
(Continued)

(56) References Cited

U.S. PATENT DOCUMENTS

| 3,605,123 A | 9/1971 | Hahn |
| 3,808,606 A | 5/1974 | Tronzo |

(Continued)

FOREIGN PATENT DOCUMENTS

| CN | 106667626 A | 5/2017 |
| DE | 837294 C | 4/1952 |

(Continued)

OTHER PUBLICATIONS

Hulbert, S.F., et al.; "Materials of Construction for Artificial Bone Segments"; Research in Dental and Medical Materials (Edward Korostoff ed., 1969), pp. 19-67.
(Continued)

*Primary Examiner* — Eric S Gibson
(74) *Attorney, Agent, or Firm* — Pearne & Gordon LLP

(57) ABSTRACT

Spinal interbody cages are provided that include a bulk interbody cage, a top face, a bottom face, a top mesh structure, a bottom mesh structure, pillars, and slots. The top and bottom faces are exterior surfaces of the bulk interbody cage having a top central opening and a bottom central opening, respectively. The top and bottom mesh structures extend from the bulk interbody cage across the top central opening and the bottom central opening, respectively. The pillars are for contacting vertebral bodies. The slots are to be occupied by bone of the vertebral bodies and/or by bone of
(Continued)

a bone graft. The spinal interbody cage has a Young's modulus of elasticity of at least 3 GPa, and has a ratio of the sum of (i) the volumes of the slots to (ii) the sum of the volumes of the pillars and the volumes of the slots of 0.40:1 to 0.90:1.

20 Claims, 31 Drawing Sheets

(52) U.S. Cl.
CPC ............ *A61F 2002/30151* (2013.01); *A61F 2002/30227* (2013.01); *A61F 2002/30892* (2013.01); *A61F 2310/00023* (2013.01); *A61F 2310/00179* (2013.01)

(58) Field of Classification Search
CPC ...... A61F 2002/3092; A61F 2002/3093; A61F 2002/4495
See application file for complete search history.

(56) References Cited

U.S. PATENT DOCUMENTS

| | | | |
|---|---|---|---|
| 3,855,638 | A | 12/1974 | Pilliar |
| 4,237,559 | A | 12/1980 | Borom |
| 4,608,052 | A | 8/1986 | Van Kampen et al. |
| 4,834,757 | A | 5/1989 | Brantigan |
| 4,865,603 | A | 9/1989 | Noiles |
| 5,195,892 | A | 3/1993 | Gersberg |
| 5,207,709 | A | 5/1993 | Picha |
| 5,236,453 | A | 8/1993 | Picha |
| 5,263,953 | A | 11/1993 | Bagby |
| 5,312,256 | A | 5/1994 | Scortecci |
| 5,545,226 | A | 8/1996 | Wingo et al. |
| 5,571,185 | A | 11/1996 | Schug |
| 5,628,630 | A | 5/1997 | Misch |
| 5,823,777 | A | 10/1998 | Misch |
| 5,876,457 | A | 3/1999 | Picha et al. |
| 6,001,100 | A | 12/1999 | Sherman et al. |
| 6,071,310 | A | 6/2000 | Picha et al. |
| 6,106,558 | A | 8/2000 | Picha |
| 6,315,562 | B1 | 11/2001 | Kumar |
| 6,346,122 | B1 | 2/2002 | Picha et al. |
| 6,470,036 | B1 | 10/2002 | Bailey et al. |
| 6,569,201 | B2 | 5/2003 | Moumene et al. |
| 6,672,940 | B1 | 1/2004 | Graham |
| 6,789,991 | B2 | 9/2004 | Hsu |
| 6,846,313 | B1 | 1/2005 | Rogers et al. |
| 6,900,302 | B2 | 5/2005 | Teti |
| 6,989,032 | B2 | 1/2006 | Errico et al. |
| 7,018,418 | B2 | 3/2006 | Amrich et al. |
| 7,041,140 | B2 | 5/2006 | Picha |
| 7,128,760 | B2 | 10/2006 | Michelson |
| 7,205,051 | B2 | 4/2007 | King et al. |
| 7,250,550 | B2 | 7/2007 | Overby et al. |
| 7,347,873 | B2 | 3/2008 | Paul et al. |
| 7,393,170 | B2 | 7/2008 | Chen |
| 7,556,648 | B2 | 7/2009 | Picha et al. |
| 7,608,107 | B2 | 10/2009 | Michelson |
| 7,691,148 | B2 | 4/2010 | Michelson |
| 7,955,512 | B2 | 6/2011 | Park et al. |
| 8,551,173 | B2 * | 10/2013 | Lechmann ............ A61F 2/44 623/17.12 |
| 8,685,070 | B2 | 4/2014 | Rupp et al. |
| 8,764,831 | B2 | 7/2014 | Lechmann et al. |
| 8,771,354 | B2 * | 7/2014 | Picha ............ A61L 27/06 623/16.11 |
| 9,198,701 | B2 | 12/2015 | Prien et al. |
| 9,333,081 | B2 * | 5/2016 | Picha ............ A61C 8/0037 |
| 9,456,856 | B2 | 10/2016 | Ballard |
| 9,579,206 | B2 * | 2/2017 | Picha ............ A61L 27/3612 |
| 9,581,183 | B2 | 2/2017 | Lajewardi et al. |
| 9,801,673 | B2 | 10/2017 | Aeschlimann et al. |
| 9,808,346 | B2 | 11/2017 | Stark |
| 10,154,908 | B2 * | 12/2018 | Picha ............ A61L 27/18 |
| 11,123,173 | B2 * | 9/2021 | Picha ............ A61F 2/0077 |
| 2001/0039454 | A1 | 11/2001 | Ricci et al. |
| 2002/0040242 | A1 | 4/2002 | Picha et al. |
| 2002/0106393 | A1 | 8/2002 | Bianchi et al. |
| 2004/0093028 | A1 | 5/2004 | Ruff |
| 2004/0122518 | A1 | 6/2004 | Rhoda |
| 2004/0181286 | A1 | 9/2004 | Michelson |
| 2004/0260291 | A1 | 12/2004 | Jensen |
| 2005/0033289 | A1 | 2/2005 | Warren et al. |
| 2005/0049706 | A1 | 3/2005 | Brodke et al. |
| 2005/0112397 | A1 * | 5/2005 | Rolfe ............ A61F 2/0811 428/593 |
| 2005/0246021 | A1 | 11/2005 | Ringeisen et al. |
| 2005/0283158 | A1 | 12/2005 | West |
| 2006/0015184 | A1 | 1/2006 | Winterbottom et al. |
| 2006/0030884 | A1 | 2/2006 | Yeung |
| 2007/0123988 | A1 | 5/2007 | Coughlin |
| 2007/0166124 | A1 | 7/2007 | Hsu |
| 2007/0168037 | A1 | 7/2007 | Posnick |
| 2008/0109037 | A1 | 5/2008 | Steiner |
| 2008/0147098 | A1 * | 6/2008 | Trieu ............ A61F 2/442 606/151 |
| 2008/0183292 | A1 * | 7/2008 | Trieu ............ A61F 2/442 623/17.11 |
| 2008/0287910 | A1 | 11/2008 | Picha |
| 2008/0306554 | A1 | 12/2008 | Mckinley |
| 2009/0069904 | A1 | 3/2009 | Picha |
| 2009/0105772 | A1 | 4/2009 | Seebeck |
| 2009/0204214 | A1 | 8/2009 | Fuji et al. |
| 2010/0042167 | A1 | 2/2010 | Nebosky et al. |
| 2010/0211118 | A1 | 8/2010 | Christen et al. |
| 2010/0256758 | A1 | 10/2010 | Gordon et al. |
| 2010/0298950 | A1 * | 11/2010 | McDonnell ......... A61F 2/30771 623/23.53 |
| 2011/0093020 | A1 | 4/2011 | Wu |
| 2011/0125264 | A1 | 5/2011 | Bagga et al. |
| 2011/0213467 | A1 | 9/2011 | Lozier et al. |
| 2011/0218585 | A1 | 9/2011 | Krinke et al. |
| 2011/0320000 | A1 | 12/2011 | O'Neil et al. |
| 2012/0271427 | A1 | 10/2012 | Serafin |
| 2013/0090735 | A1 | 4/2013 | Mermuys et al. |
| 2013/0110241 | A1 | 5/2013 | Palmatier et al. |
| 2013/0116793 | A1 * | 5/2013 | Kloss ............ A61F 2/4455 623/17.16 |
| 2013/0325129 | A1 * | 12/2013 | Huang ............ A61F 2/2803 623/17.16 |
| 2014/0025181 | A1 | 1/2014 | Vanasse et al. |
| 2014/0180432 | A1 | 6/2014 | Conway et al. |
| 2014/0303729 | A1 | 10/2014 | Lee |
| 2015/0305878 | A1 | 10/2015 | O'Neil et al. |
| 2016/0067048 | A1 | 3/2016 | Hensley et al. |
| 2016/0213475 | A1 * | 7/2016 | Picha ............ A61F 2/30756 |
| 2017/0119530 | A1 * | 5/2017 | Picha ............ A61L 27/06 |
| 2019/0254840 | A1 * | 8/2019 | Gray ............ A61F 2/4455 |
| 2020/0323646 | A1 * | 10/2020 | Picha ............ A61F 2/447 |
| 2021/0085481 | A1 * | 3/2021 | Cain ............ A61F 2/4455 |
| 2021/0154023 | A1 * | 5/2021 | Picha ............ A61F 2/30771 |

FOREIGN PATENT DOCUMENTS

| | | |
|---|---|---|
| DE | 33 22 803 A1 | 1/1985 |
| DE | 103 25 139 A1 | 12/2004 |
| EP | 0 162 604 A1 | 11/1985 |
| EP | 0 269 256 A1 | 6/1988 |
| EP | 2 253 291 A1 | 11/2010 |
| FR | 3 019 032 A1 | 10/2015 |
| GB | 2 181 354 A | 4/1987 |
| WO | 96/40015 A1 | 12/1996 |
| WO | 96/40020 A1 | 12/1996 |
| WO | 2002017823 A1 | 3/2002 |
| WO | 2002032345 A2 | 4/2002 |
| WO | 2007/113862 A1 | 10/2007 |
| WO | 2008/070355 A2 | 6/2008 |
| WO | 2009022911 A2 | 2/2009 |
| WO | 2009/034429 A2 | 3/2009 |
| WO | 2009108789 A1 | 9/2009 |

(56) References Cited

FOREIGN PATENT DOCUMENTS

| WO | 2013063069 A1 | 5/2013 |
| WO | 2016018160 A1 | 2/2016 |
| WO | 2016/029254 A1 | 3/2016 |
| WO | 2016082880 A1 | 6/2016 |
| WO | 2016/130878 A1 | 8/2016 |
| WO | 2018/053403 A1 | 3/2018 |
| WO | 2018/165405 A1 | 9/2018 |
| WO | 2018165400 A1 | 9/2018 |
| WO | 2018165403 A1 | 9/2018 |
| WO | 2018169929 A1 | 9/2018 |

OTHER PUBLICATIONS

Bobyn, et al.; "Characteristics of bone ingrowth and interface mechanics of a new porous tantalum biomaterial"; The Journal of Bone & Joint Surgery (Br); vol. 81-B, No. 5; Sep. 1999; pp. 907-914.

Tala, A.I., et al.; "Pore Diameter of More Than 100 μm Is Not Requisite for Bone Ingrowth in Rabbits"; 58 Journal of Biomedical Materials Research (Applied Biomaterials); 2001; pp. 679-683.

Briem, D., et al.; "Response of primary fibroblasts and osteoblasts to plasma treated polyetheretherketone (PEEK) surfaces"; 16 Journal of Materials Science Materials in Medicine; 2005; pp. 671-677.

Biomechanics, BME 315; "Elastic anisotropy of bone" (http://silver.neep.wisc.edu/~lakes/BME315N3.pdf—accessed Dec. 8, 2010); p. 1.

Dai, K., "Rational Utilization of the Stress Shielding Effect of Implants"; Biomechanics and Biomaterials in Orthopedics ed. Dominique G. Poitout, Springer-Verlag London Limited, Singapore, 2004); pages: title, copyright, and 208-215.

McPherson, E.J., "Adult Reconstruction"; Review of Orthopaedics: Expert Consult; Fifth Edition (ed. Mark D. Miller, Saunders Elsevier, U.S., 2008); pp. 312-313, Section 4; "Complications in fixation," subsection a, "Stress shielding."

International Search Report and Written Opinion for corresponding International Application No. PCT/US2019/026613 dated Jul. 9, 2019, 10 pages.

Bobyn et al., "The Optimum Pore Size for the Fixation of Porous-Surfaced Metal Implants by the Ingrowth of Bone," Clinical Orthopaedics and Related Research, No. 150, pp. 263-270 (1980).

Jain et al., "Advances in Spinal Interbody Cages," Orthop. Surg., vol. 8, p. 278 (abstract only) (Aug. 2016).

Chong et al., "The design evolution of interbody cages in anterior cervical discectomy and fusion: a systematic review," BMC Musculoskeletal Disorders, DOI 10.1186/s12891-015-0546-x, pp. 1-11 (Apr. 25, 2015).

Pawtex, "ConnectSPINE TM) PPM (TM) (Porous Paw Metal) Anterior Cervical Interbody Fusion Case (ACIF)," pp. 1-2, available at http://www.cusmed.com/porous-paw-metal-anterior-cervical-interbody-fusion-cage.html, last accessed Mar. 7, 2018.

Zimmer Biomet, "TM-S Cervial Fusion Device," pp. 1-11, available at http://www.zimmerbiomet.com/medical-professionals/spine/product/tm-s-device.html; last accessed Mar. 7, 2018.

Dolton et al., "Screws-Form and Function," AOTrauma (Nov. 2012), pp. 1-10.

Extended European Search Report dated Dec. 17, 2021 for corresponding European Application No. 19785193.4, pp. 1-10.

* cited by examiner

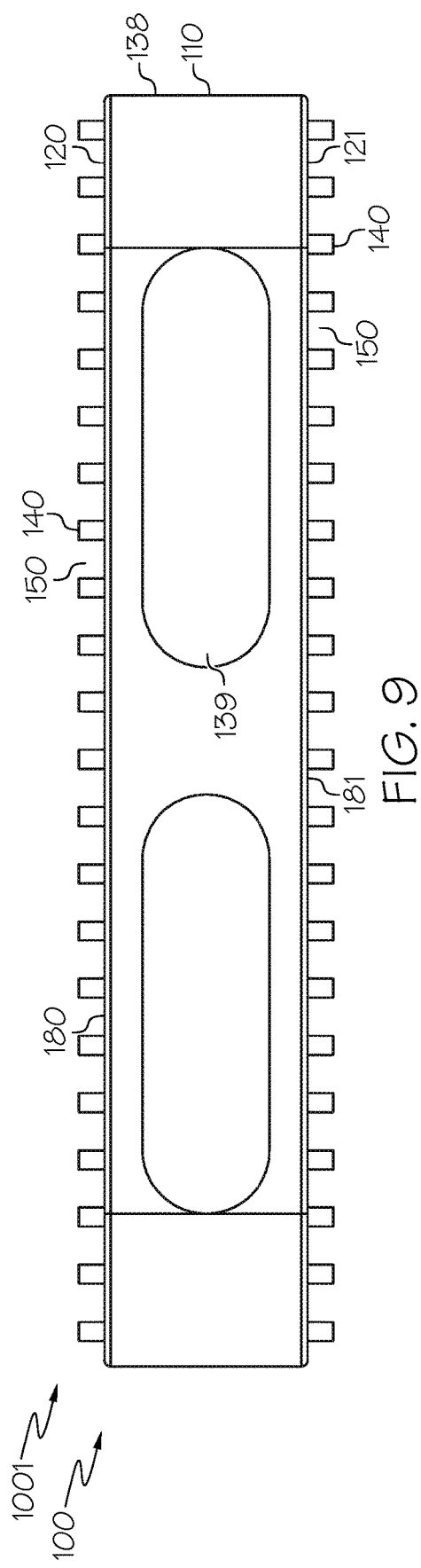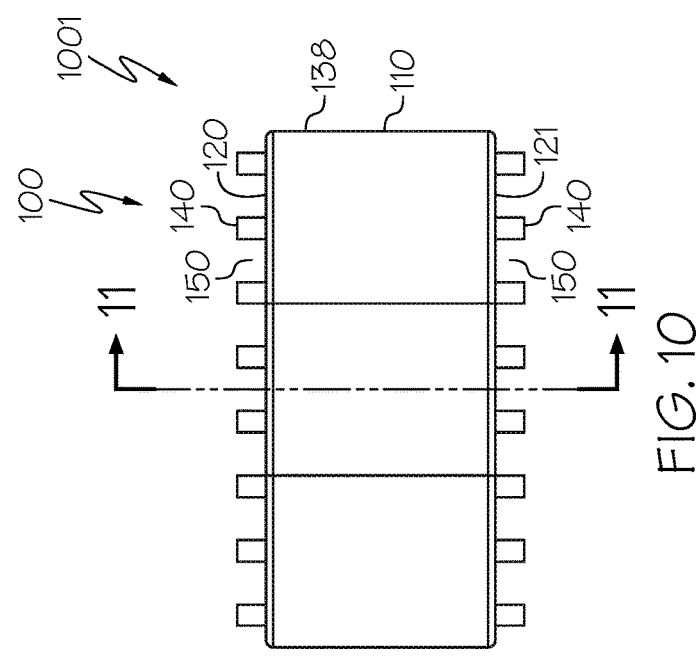
FIG. 9
FIG. 10

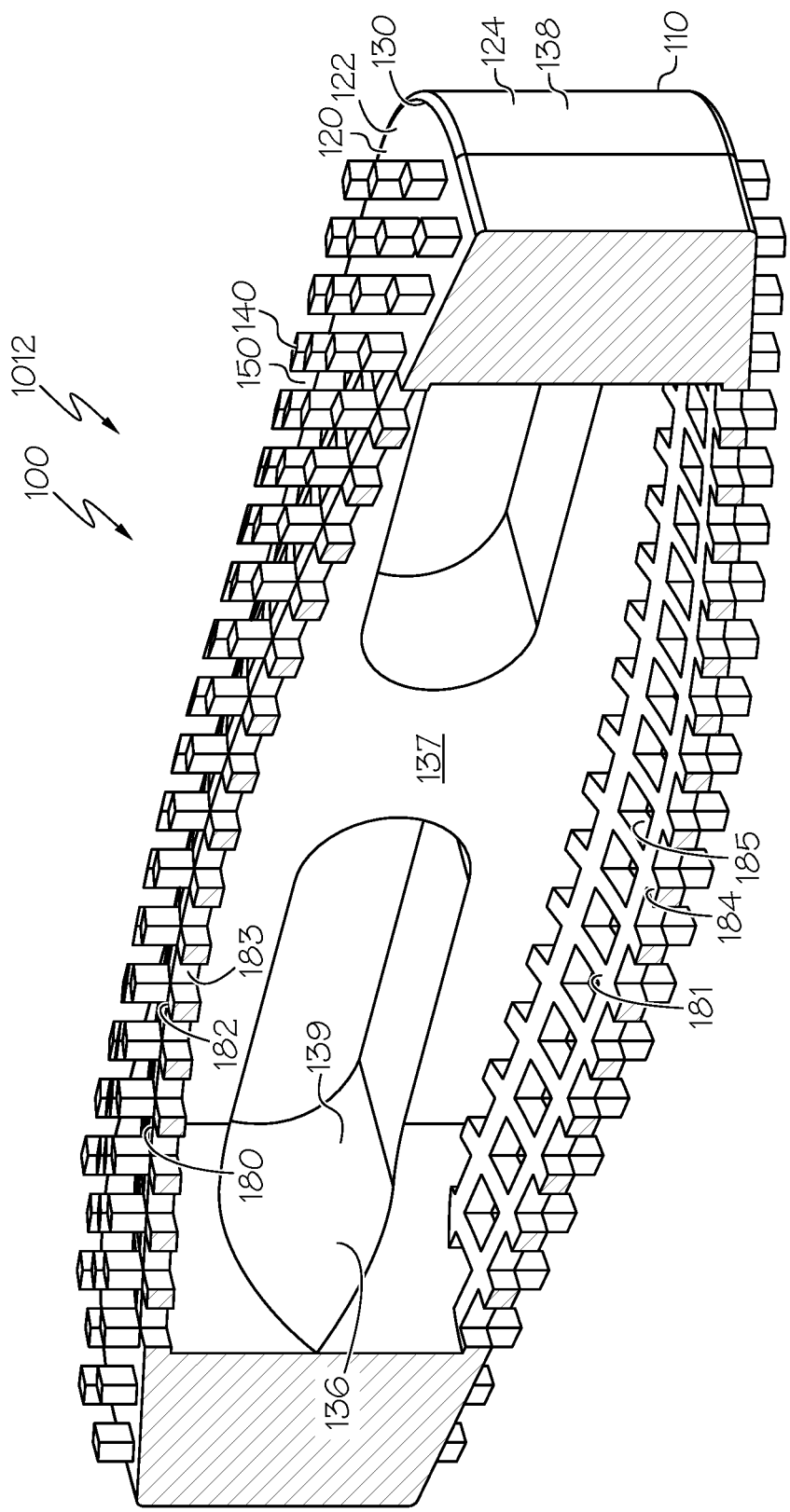

SPINAL INTERBODY CAGE COMPRISING TOP AND BOTTOM FACES WITH MESH STRUCTURES, PILLARS AND SLOTS

CROSS-REFERENCE TO RELATED APPLICATIONS

This application claims the benefit of U.S. Provisional Application No. 62/655,418, filed Apr. 10, 2018, the entire disclosure of which is hereby incorporated by reference.

FIELD OF THE INVENTION

The invention relates to spinal interbody cages, and more particularly to spinal interbody cages that include a bulk interbody cage, a top face, a bottom face, a top mesh structure, a bottom mesh structure, pillars, and slots.

BACKGROUND OF THE INVENTION

Conventional hard-tissue implants include implants designed to promote ingrowth of hard tissue based on forming a tissue/implant interface in which the implant forms a continuous phase and the tissue forms a discontinuous phase, e.g. based on the implant having a concave and/or porous surface into which the hard tissue can grow, and designed to have add-on surface modifications, e.g. modifications added based on sintering.

For example, Van Kampen et al., U.S. Pat. No. 4,608,052, discloses an implant for use in a human body having an integral attachment surface adapted to permit ingrowth of living tissue. The implant surface is defined by a multiplicity of adjacent, generally concave surface parts having intersecting, generally aligned rims defining an inner attachment surface portion and by a multiplicity of spaced posts projecting from the inner attachment surface. Van Kampen also discloses that implants have been provided with porous surfaces, as described in U.S. Pat. Nos. 3,605,123, 3,808, 606, and 3,855,638.

Also for example, J. D. Bobyn et al, 150 Clinical Orthopaedics & Related Research 263 (1980), discloses that a pore size range of approximately 50 to 400 µm provided an optimal or maximal fixation strength (17 MPa) in the shortest time period (8 weeks) with regard to cobalt-base alloy implants with powder-made porous surfaces. Specifically, implants were fabricated based on coating cylindrical rods of cast cobalt-base alloy with cobalt base alloy powder in four particle size ranges. The particle size ranges were as follows: 25 to 45 µm; 45 to 150 µm; 150 to 300 µm; and 300 to 840 µm. The corresponding pore size ranges of the particles were as follows: 20 to 50 µm; 50 to 200 µm; 200 to 400 µm; and 400 to 800 µm, respectively. The particles were then bonded to the rods based on sintering. All implants were manufactured to have a maximal diameter of 4.5 mm and a length of 9.0 mm. The implants were surgically inserted into holes in dog femurs and bone ingrowth was allowed to proceed. After varying periods of time (4, 8, or 12 weeks), the maximum force required to dislodge the implants was determined. Implants with a pore size lower than 50 µm yielded relatively low fixation strengths at all time points, while implants with a pore size higher than 400 µm exhibited relatively high scatter with regard to fixation strengths, thus indicating that a pore size range of approximately 50 to 400 µm provided an optimal or maximal fixation strength.

Conventional hard-tissue implants also include implants having surface texturing, e.g. raised portions and indented portions, barbs, and/or pillars, to promote an interference fit between the implants and adjacent bone, to make it difficult to withdraw the implants from hard tissue, or to more effectively mechanically anchor at an early date or affix into adjoining hard tissue.

For example, Tuke et al., U.K. Pat. Appl. No. GB2181354A, discloses an orthopedic implant having at least one surface area, integral with the adjacent portion of the implant and adapted in use to contact bone. The surface area has a finely patterned conformation composed of a plurality of raised portions separated from each other by indented portions. The indented portions are of a width and depth to allow bone penetration thereinto in use to promote an interference fit between the implant and adjacent bone in the region of the patterned area.

Also for example, Amrich et al., U.S. Pat. No. 7,018,418, discloses implants having a textured surface with microrecesses such that the outer surface overhangs the microrecesses. In one embodiment, unidirectional barbs are produced in the surface that can be inserted into bone or tissue. The directional orientation of the barbs is intended to make it difficult to withdraw from the bone or tissue.

Also for example, Picha, U.S. Pat. No. 7,556,648, discloses a spinal implant, i.e. an implant for use in fusing and stabilizing adjoining spinal vertebrae, including a hollow, generally tubular shell having an exterior lateral surface, a leading end, and a trailing end. The exterior surface includes a plurality of pillars arranged in a non-helical array. Each pillar has a height of 100 to 4,500 µm and a lateral dimension at the widest point of 100 to 4,500 µm. The exterior surface also has a plurality of holes therethrough to permit bone ingrowth therethrough.

Also for example, Paul et al., U.S. Pat. No. 7,347,873, discloses an allogenic intervertebral implant for fusing vertebrae. The implant has a wedge-shaped profile to restore disc height and the natural curvature of the spine. The top and bottom surfaces of the implant have a plurality of teeth to resist expulsion and provide initial stability.

Also for example, Lechmann et al., U.S. Pat. No. 8,764, 831, discloses an intervertebral implant that includes a three-dimensional body in the form of a cage with an upper side and an underside, which are suitable for abutting the end plates of two adjacent vertebral bodies. The upper side and the underside of the three-dimensional body are provided with structuring in the form of teeth.

Also for example, Ballard, U.S. Pat. No. 9,456,856, discloses an intrabody implant for placement between separated portions of a previously-unitary bony structure, such as a vertebral body. The intrabody implant comprises first and second surfaces for engaging the first and second portions of the separated bony structure. The first and second surfaces may comprise a plurality of surface features extending outward from the surfaces to engage a complementary surface of the bony structure. The surface features can include ridges, teeth, pyramidal structures, roughened irregular projections and/or combinations thereof.

Also for example, Rhoda, U.S. Pub. No. 2004/0122518, discloses a vertebral implant for fusing adjacent vertebrae or for replacing vertebral bodies. The implant is a biocompatible metal, resorbable, or radiolucent implant conforming substantially in size and shape with an end plate of a vertebra. The implant preferably has a wedge-shaped profile to restore disc height and the natural curvature of the spine. The top and bottom surfaces of the implant have areas with a plurality of teeth to resist expulsion and provide initial stability and areas devoid of any protrusions to receive implantation instrumentation.

Unfortunately, interfaces of hard tissue and hard-tissue implants in which the hard tissue is in a discontinuous phase may be susceptible to stress shielding, resulting in resorption of affected hard tissue, e.g. bone resorption, over time. Also, addition of surface texturing to implants by sintering can result in the surface texturing occupying an excessive volume of corresponding hard tissue/implant interfaces, leaving insufficient space for hard tissue. In addition, implants for hard tissues such as long bone, maxillary bone, mandibular bone, and membranous bone are designed to perform under conditions relevant to those hard tissues, i.e. load bearing conditions, including compression and tension, varying across the hard tissue and across time, and intermittent rotational and vertical shear, rather than conditions relevant to spine, i.e. compression, rotational shear, and vertical shear, with the compression being essentially constant, the rotational shear being intermittent, and the vertical shear being rare.

Picha et al., U.S. Pat. No. 8,771,354, discloses hard-tissue implants including a bulk implant, a face, pillars, and slots. The hard-tissue implant has a Young's modulus of elasticity of at least 10 GPa, has a ratio of (i) the sum of the volumes of the slots to (ii) the sum of the volumes of the pillars and the volumes of the slots of 0.40:1 to 0.90:1, does not comprise any part that is hollow, and does not comprise any non-pillar part extending to or beyond the distal ends of any of the pillars. The hard-tissue implants can provide immediate load transfer upon implantation and prevent stress shielding over time, thus promoting hard-tissue remodeling and growth at the site of implantation. The interface can have a continuous phase corresponding to the hard tissue and a discontinuous phase corresponding to the hard-tissue implant.

Nonetheless, there remains a need for hard-tissue implants that address the issues discussed above and that provide improvements. The spinal interbody cage disclosed herein is such an implant.

BRIEF SUMMARY OF THE INVENTION

A spinal interbody cage is provided that includes a bulk interbody cage, a top face, a bottom face, a top mesh structure, a bottom mesh structure, pillars, and slots.

The top face is a top exterior surface of the bulk interbody cage and has a top central opening. The bottom face is a bottom exterior surface of the bulk interbody cage and has a bottom central opening.

The top mesh structure extends from the bulk interbody cage across the top central opening, comprises top mesh links, and has top mesh openings between the top mesh links. Each top mesh link has a width of 100 to 2,000 μm. Each top mesh opening has a mesh opening area of (100× 100) to (2,500×2,500) μm². The bottom mesh structure extends from the bulk interbody cage across the bottom central opening, comprises bottom mesh links, and has bottom mesh openings between the bottom mesh links. Each bottom mesh link has a width of 100 to 2,000 μm. Each bottom mesh opening has a mesh opening area of (100×100) to (2,500×2,500) μm².

The pillars are for contacting vertebral bodies. The pillars are distributed on the top face, the bottom face, the top mesh structure, and the bottom mesh structure, and extend distally therefrom, across areas of at least 25 mm² of each of the top face, the bottom face, the top mesh structure, and the bottom mesh structure. Each pillar that extends from the top face or the bottom face is integral to the bulk interbody cage. Each pillar that extends from the top mesh structure or the bottom mesh structure is integral to the top mesh structure or the bottom mesh structure, respectively. Each pillar has a distal end, a transverse area of (100×100) to (2,000×2,000) μm², and a height of 100 to 2,500 μm.

The slots are to be occupied by bone of the vertebral bodies and/or by bone of a bone graft. The slots are defined by the pillars. The slots intersect between the pillars. Each slot has a width of 100 to 2,500 μm as measured along the shortest distance between adjacent pillars.

The spinal interbody cage has a Young's modulus of elasticity of at least 3 GPa, and has a ratio of (i) the sum of the volumes of the slots to (ii) the sum of the volumes of the pillars and the volumes of the slots of 0.40:1 to 0.90:1.

In some examples, the spinal interbody cage is made of one or more materials selected from implantable-grade polyaryletherketone that is essentially unfilled, implantable-grade polyetheretherketone, implantable-grade polyetherketoneketone, titanium, stainless steel, cobalt-chromium alloy, titanium alloy, Ti-6Al-4V titanium alloy, Ti-6Al-7Nb titanium alloy, ceramic material, silicon nitride (Si3N4), implantable-grade composite material, implantable-grade polyaryletherketone with filler, implantable-grade polyetheretherketone with filler, implantable-grade polyetheretherketone with carbon fiber, or implantable-grade polyetheretherketone with hydroxyapatite.

In some examples, the spinal interbody cage is made of one or more other hard tissues selected from human hard tissue, animal hard tissue, autologous hard tissue, allogenic hard tissue, xenogeneic hard tissue, human cartilage, animal cartilage, human bone, animal bone, cadaver bone, or cortical allograft.

In some examples, the spinal interbody cage is made of one or more materials selected from resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic.

In some examples, the spinal interbody cage has a parallel profile. Also in some examples, the spinal interbody cage has a lordotic profile. Also in some examples, the spinal interbody cage has a domed profile.

In some examples, the pillars extend in a uniform direction. Also in some examples, one or more pillars extend at an angle and/or in a direction that differs from that of other pillars.

In some examples, a plurality of the pillars are perpendicular to the top face, a plurality of the pillars are perpendicular to the bottom face, a plurality of the pillars are perpendicular to the top mesh structure, and a plurality of the pillars are perpendicular to the bottom mesh structure.

In some examples, each top mesh link and bottom mesh link has a width of 250 to 1,000 μm. In some examples, each top mesh opening and bottom mesh opening has a mesh opening area of (150×150) to (1,000×1,000) μm².

In some examples, the transverse area of each pillar is (250×250) μm² to (1,000×1,000) μm². In some examples, the height of each pillar is 300 to 1,000 μm. In some examples, the width of each slot is 150 to 1,000 μm.

In some examples, the Young's modulus of the spinal interbody cage is 18 to 25 GPa and the ratio of (i) the sum of the volumes of the slots to (ii) the sum of the volumes of the pillars and the volumes of the slots is 0.51:1 to 0.60:1. Also in some examples, the Young's modulus of the spinal interbody cage is 100 to 110 GPa and the ratio of (i) the sum of the volumes of the slots to (ii) the sum of the volumes of the pillars and the volumes of the slots is 0.72:1 to 0.76:1. Also in some examples, the spinal interbody cage is made of implantable-grade polyetheretherketone with filler, the transverse area of each pillar is (350× 350) to (450×450) µm², the height of each pillar is 400 to 600 µm, the width of each slot is 190 to 210 µm, and the ratio of the sum of (i) the volumes of the slots to (ii) the sum of the volumes of the pillars and the volumes of the slots is 0.51:1 to 0.60:1. Also in some examples, the spinal interbody cage is made of titanium, the transverse area of each pillar is (350×350) to (450×450) µm², the height of each pillar is 400 to 600 µm, the width of each slot is 390 to 410 µm, and the ratio of (i) the sum of the volumes of the slots to (ii) the sum of the volumes of the pillars and the volumes of the slots is 0.72:1 to 0.76:1.

In some examples, the bulk interbody cage is non-porous. In some examples, the top mesh structure and the bottom mesh structure are non-porous. In some examples, the pillars are non-porous.

In some examples, one or more pillars have dimensions that differ from those of other pillars, such that the transverse areas and/or heights, and thus volumes, of the one or more pillars differ from those of the other pillars. In some of these examples, the spinal interbody cage provides an endplate profile based on the heights of the one or more pillars differing from those of the other pillars, and the spinal interbody cage having a parallel height.

In some examples, the pillars are distributed and dimensioned to provide immediate micro-subsidence following implantation in a patient, between adjacent vertebral bodies, thereby providing post-operative interdigitated fixation and stability.

In some examples, the spinal interbody cage comprises at least one lateral exterior surface. In some of these examples, the at least one lateral exterior surface includes one or more lateral surface openings. Also in some of these examples, the at least one lateral exterior surface comprises pillars extending from the at least one lateral exterior surface.

In some examples, the spinal interbody cage comprises at least one interior surface comprising pillars extending from the least one interior surface. In some of these examples, one or more of the pillars extending from the at least one interior surface have heights that differ from those of other pillars extending from the at least one interior surface.

In some examples, the pillars comprise, at their distal ends, a roughened surface.

In some examples, the transverse area of one or more of the pillars increases distally. Also in some examples, the transverse area of one or more of the pillars does not decrease distally. Also in some examples, the transverse area of one or more of the pillars is substantially constant along the vertical axis along which the one or more pillars extend distally.

In some examples, the top mesh structure and the bottom mesh structure are integral to the bulk interbody cage.

In some examples, the spinal interbody cage is selected from the group consisting of an anterior lumbar interbody fusion (ALIF) spinal interbody cage, a posterior lumbar interbody fusion (PLIF) spinal interbody cage, a lateral spinal interbody cage, a direct lateral interbody fusion (DLIF) spinal interbody cage, a transforaminal lumbar interbody fusion (TLIF) spinal interbody cage, an extreme lateral interbody fusion (XLIF) spinal interbody cage, and a cervical spinal interbody cage.

Exemplary embodiments include the following:

Embodiment 1: A spinal interbody cage comprising: (a) a bulk interbody cage; (b) a top face being a top exterior surface of the bulk interbody cage and having a top central opening; (c) a bottom face being a bottom exterior surface of the bulk interbody cage and having a bottom central opening; (d) a top mesh structure extending from the bulk interbody cage across the top central opening, comprising top mesh links, and having top mesh openings between the top mesh links, each top mesh link having a width of 100 to 2,000 µm, and each top mesh opening having a mesh opening area of (100×100) to (2,500×2,500) µm²; (e) a bottom mesh structure extending from the bulk interbody cage across the bottom central opening, comprising bottom mesh links, and having bottom mesh openings between the bottom mesh links, each bottom mesh link having a width of 100 to 2,000 µm, and each bottom mesh opening having a mesh opening area of (100×100) to (2,500×2,500) µm²; (f) pillars for contacting vertebral bodies, the pillars being distributed on the top face, the bottom face, the top mesh structure, and the bottom mesh structure, and extending distally therefrom, across areas of at least 25 mm² of each of the top face, the bottom face, the top mesh structure, and the bottom mesh structure, each pillar that extends from the top face or the bottom face being integral to the bulk interbody cage, each pillar that extends from the top mesh structure or the bottom mesh structure being integral to the top mesh structure or the bottom mesh structure, respectively, and each pillar having a distal end, a transverse area of (100× 100) to (2,000×2,000) µm², and a height of 100 to 2,500 µm; and (g) slots to be occupied by bone of the vertebral bodies and/or by bone of a bone graft, the slots being defined by the pillars, the slots intersecting between the pillars, and each slot having a width of 100 to 2,500 µm as measured along the shortest distance between adjacent pillars; wherein the spinal interbody cage has a Young's modulus of elasticity of at least 3 GPa, and has a ratio of (i) the sum of the volumes of the slots to (ii) the sum of the volumes of the pillars and the volumes of the slots of 0.40:1 to 0.90:1.

Embodiment 2: The spinal interbody cage of embodiment 1, wherein the spinal interbody cage is made of one or more materials selected from implantable-grade polyaryletherketone that is essentially unfilled, implantable-grade polyetheretherketone, implantable-grade polyetherketoneketone, titanium, stainless steel, cobalt-chromium alloy, titanium alloy, Ti-6Al-4V titanium alloy, Ti-6Al-7Nb titanium alloy, ceramic material, silicon nitride (Si3N4), implantable-grade composite material, implantable-grade polyaryletherketone with filler, implantable-grade polyetheretherketone with filler, implantable-grade polyetheretherketone with carbon fiber, or implantable-grade polyetheretherketone with hydroxyapatite.

Embodiment 3: The spinal interbody cage of embodiment 1 or embodiment 2, wherein the spinal interbody cage is made of one or more other hard tissues selected from human hard tissue, animal hard tissue, autologous hard tissue, allogenic hard tissue, xenogeneic hard tissue, human cartilage, animal cartilage, human bone, animal bone, cadaver bone, or cortical allograft.

Embodiment 4: The spinal interbody cage of any one of embodiments 1-3, wherein the spinal interbody cage is made of one or more materials selected from resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic.

Embodiment 5: The spinal interbody cage of any one of embodiments 1-4, wherein the spinal interbody cage has a parallel profile.

Embodiment 6: The spinal interbody cage of any one of embodiments 1-4, wherein the spinal interbody cage has a lordotic profile.

Embodiment 7: The spinal interbody cage of any one of embodiments 1-4, wherein the spinal interbody cage has a domed profile.

Embodiment 8: The spinal interbody cage of any one of embodiments 1-7, wherein the pillars extend in a uniform direction.

Embodiment 9: The spinal interbody cage of any one of embodiments 1-7, wherein one or more pillars extend at an angle and/or in a direction that differs from that of other pillars.

Embodiment 10: The spinal interbody cage of any one of embodiments 1-9, wherein a plurality of the pillars are perpendicular to the top face, a plurality of the pillars are perpendicular to the bottom face, a plurality of the pillars are perpendicular to the top mesh structure, and a plurality of the pillars are perpendicular to the bottom mesh structure.

Embodiment 11: The spinal interbody cage of any one of embodiments 1-10, wherein each top mesh link and bottom mesh link has a width of 250 to 1,000 µm.

Embodiment 12: The spinal interbody cage of any one of embodiments 1-11, wherein each top mesh opening and bottom mesh opening has a mesh opening area of (150× 150) to (1,000×1,000) µm².

Embodiment 13: The spinal interbody cage of any one of embodiments 1-12, wherein the transverse area of each pillar is (250×250) µm² to (1,000×1,000) µm².

Embodiment 14: The spinal interbody cage of any one of embodiments 1-13, wherein the height of each pillar is 300 to 1,000 µm.

Embodiment 15: The spinal interbody cage of any one of embodiments 1-14, wherein the width of each slot is 150 to 1,000 µm.

Embodiment 16: The spinal interbody cage of any one of embodiments 1-15, wherein the Young's modulus of the spinal interbody cage is 18 to 25 GPa and the ratio of (i) the sum of the volumes of the slots to (ii) the sum of the volumes of the pillars and the volumes of the slots is 0.51:1 to 0.60:1.

Embodiment 17: The spinal interbody cage of any one of embodiments 1-15, wherein the Young's modulus of the spinal interbody cage is 100 to 110 GPa and the ratio of (i) the sum of the volumes of the slots to (ii) the sum of the volumes of the pillars and the volumes of the slots is 0.72:1 to 0.76:1.

Embodiment 18: The spinal interbody cage of any one of embodiments 1-15, wherein the spinal interbody cage is made of implantable-grade polyetheretherketone with filler, the transverse area of each pillar is (350×350) to (450×450) µm², the height of each pillar is 400 to 600 µm, the width of each slot is 190 to 210 µm, and the ratio of the sum of (i) the volumes of the slots to (ii) the sum of the volumes of the pillars and the volumes of the slots is 0.51:1 to 0.60:1.

Embodiment 19: The spinal interbody cage of any one of embodiments 1-15, wherein the spinal interbody cage is made of titanium, the transverse area of each pillar is (350×350) to (450×450) µm², the height of each pillar is 400 to 600 µm, the width of each slot is 390 to 410 µm, and the ratio of (i) the sum of the volumes of the slots to (ii) the sum of the volumes of the pillars and the volumes of the slots is 0.72:1 to 0.76:1.

Embodiment 20: The spinal interbody cage of any one of embodiments 1-19, wherein the bulk interbody cage is non-porous.

Embodiment 21: The spinal interbody cage of any one of embodiments 1-20, wherein the top mesh structure and the bottom mesh structure are non-porous.

Embodiment 22: The spinal interbody cage of any one of embodiments 1-21, wherein the pillars are non-porous.

Embodiment 23: The spinal interbody cage of any one of embodiments 1-22, wherein one or more pillars have dimensions that differ from those of other pillars, such that the transverse areas and/or heights, and thus volumes, of the one or more pillars differ from those of the other pillars.

Embodiment 24: The spinal interbody cage of embodiment 23, wherein the spinal interbody cage provides an endplate profile based on the heights of the one or more pillars differing from those of the other pillars, and the spinal interbody cage having a parallel height.

Embodiment 25: The spinal interbody cage of any one of embodiments 1-24, wherein the pillars are distributed and dimensioned to provide immediate micro-subsidence following implantation in a patient, between adjacent vertebral bodies, thereby providing post-operative interdigitated fixation and stability.

Embodiment 26: The spinal interbody cage of any one of embodiments 1-25, wherein the spinal interbody cage comprises at least one lateral exterior surface.

Embodiment 27: The spinal interbody cage of embodiment 26, wherein the at least one lateral exterior surface includes one or more lateral surface openings.

Embodiment 28: The spinal interbody cage of embodiment 26 and embodiment 27, wherein the at least one lateral exterior surface comprises pillars extending from the at least one lateral exterior surface.

Embodiment 29: The spinal interbody cage of any one of embodiments 1-28, wherein the spinal interbody cage comprises at least one interior surface comprising pillars extending from the least one interior surface.

Embodiment 30: The spinal interbody cage of embodiment 29, wherein one or more of the pillars extending from the at least one interior surface have heights that differ from those of other pillars extending from the at least one interior surface.

Embodiment 31: The spinal interbody cage of any one of embodiments 1-30, wherein the pillars comprise, at their distal ends, a roughened surface.

Embodiment 32: The spinal interbody cage of any one of embodiments 1-31, wherein the transverse area of one or more of the pillars increases distally.

Embodiment 33: The spinal interbody cage of any one of embodiments 1-31, wherein the transverse area of one or more of the pillars does not decrease distally.

Embodiment 34: The spinal interbody cage of any one of embodiments 1-31, wherein the transverse area of one or more of the pillars is substantially constant along the vertical axis along which the one or more pillars extend distally.

Embodiment 35: The spinal interbody cage of any one of embodiments 1-34, wherein the top mesh structure and the bottom mesh structure are integral to the bulk interbody cage.

Embodiment 36: The spinal interbody cage of any one of embodiments 1-35, wherein the spinal interbody cage is selected from the group consisting of an anterior lumbar interbody fusion (ALIF) spinal interbody cage, a posterior lumbar interbody fusion (PLIF) spinal interbody cage, a lateral spinal interbody cage, a direct lateral interbody fusion (DLIF) spinal interbody cage, a transforaminal lumbar interbody fusion (TLIF) spinal interbody cage, an extreme lateral interbody fusion (XLIF) spinal interbody cage, and a cervical spinal interbody cage.

BRIEF DESCRIPTION OF THE DRAWINGS

These and other features, aspects, and advantages of the present disclosure are better understood when the following detailed description is read with reference to the accompanying drawings, in which:

FIG. 9 is a first side elevational view of the spinal interbody cage of FIG. 1;

FIG. 10 is a second side elevational view of the spinal interbody cage of FIG. 1;

FIG. 35 is a sectional view of the spinal interbody cage of FIG. 34.

DETAILED DESCRIPTION

Figure 1:
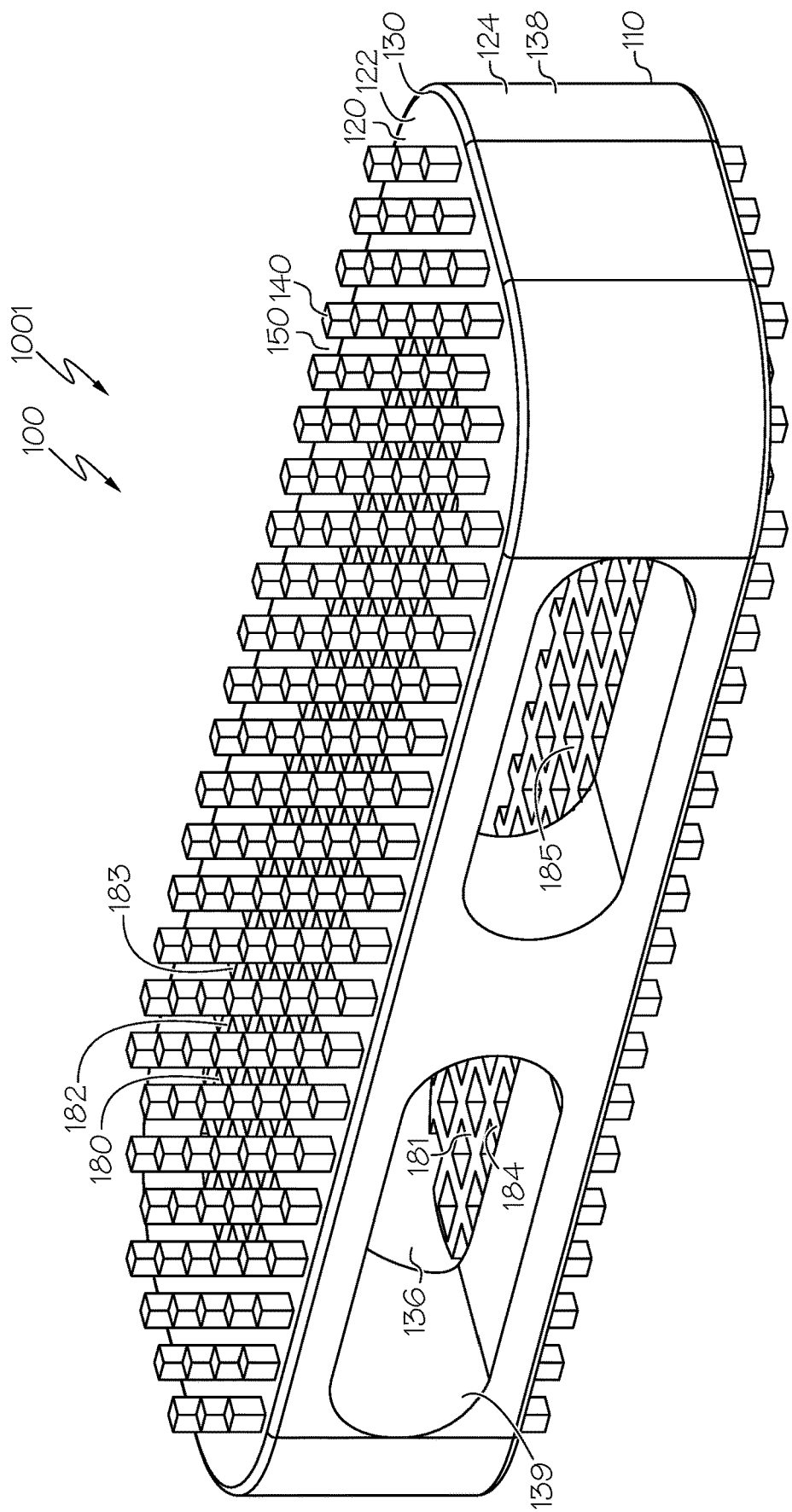
FIG. 1 is a top perspective view of an example spinal interbody cage including pillars in which the spinal interbody cage has a parallel profile and the pillars extend perpendicularly from a top face, a bottom face, a top mesh structure, and a bottom mesh structure of the spinal interbody cage and in which the pillars all have identical pillars heights.

As set forth in the figures, example spinal interbody cages are provided. The spinal interbody cages provide advantages, including for example that the spinal interbody cage can promote remodeling and growth of bone of vertebral bodies and/or bone of bone graft at a site of implantation between vertebral bodies, immediate micro-subsidence following implantation in a patient, improved fusion across an entire disc space, and improved resistance to expulsion during healing. Without wishing to be bound by theory, it is believed that these advantages are based on properties of the spinal interbody cages and the interface resulting from implantation thereof.

This is because the interface can have a continuous phase corresponding to the bone of vertebral bodies and/or bone of bone graft and a discontinuous phase corresponding to the pillars of the spinal interbody cages. The bone of vertebral bodies and/or bone of bone graft can also make up at least 40% of the volume of the interface, and the product of the Young's modulus of elasticity of the bone and the volume of the bone and the product of the Young's modulus of elasticity of the spinal interbody cage and the volume of the pillars of the spinal interbody cage can be well matched. Thus, the interface can exhibit mechanical properties similar to those of the bulk bone of the vertebral bodies adjacent to the interface. The top mesh structure and the bottom mesh structure may provide improved load distribution and decreased resorption of bone at the interface, based on providing increased surface area of the spinal interbody cages relative to spinal interbody cages with central openings that do not have mesh structures extending across the central openings. Also, the pillars of the spinal interbody cages potentially may be pressed into bone of vertebral bodies, potentially eliminating micro-motion and migration of the implant over time, accommodating torque, and/or eliminating the need for adhesives such as cement or grout to hold the spinal interbody cages in place. In addition, the spinal interbody cages may promote rich vascularization of the bone of the interface, enhancing wound healing, providing nutritional support, accelerating healing, remodeling, and integration of the bone, and limiting the potential for infection of the bone. Rapid or immediate integration of the bone into the space between the pillars of the spinal interbody cage may also prevent detrimental cellular reactions at the interface, such as formation of fibrous tissue, seroma, or thrombosis.

It is believed that implantation of the spinal interbody cage between adjacent vertebral bodies will result in the pillars of the spinal interbody cage contacting the vertebral bodies, e.g. bone of the vertebral bodies, and more particularly bone of endplates of the vertebral bodies. In some cases the pillars may initially penetrate the bone of the vertebral bodies upon implantation of the spinal interbody cage. Alternatively or additionally, in some cases the pillars may penetrate the bone of the vertebral bodies later, under physiological loading, e.g. such as when a patient in which the spinal interbody cage has been implanted stands and the spinal interbody cage thus experiences the body weight of the patient. Also alternatively or additionally, over time bone of vertebral bodies and/or bone of bone graft may grow in and around the pillars, thus occupying slots between the pillars, e.g. during healing.

It is believed that the interface resulting from implantation of the spinal interbody cage into bone of vertebral bodies will be, or can become, an interface that is continuous with respect to the bone and discontinuous with respect to the spinal interbody cage, across an area of the top face and the bottom face of the spinal interbody cage from which the pillars extend. Such an interface will exhibit properties similar to those of the bulk bone of vertebral bodies adjacent to the interface, e.g. high resilience to compression, which occurs essentially constantly, rotational shear, which occurs intermittently, and vertical shear, which occurs rarely but which is important too, providing advantages in spinal applications.

As used herein, the term "spinal interbody cage" means an implant having a cage structure, e.g. a structure having a generally cuboidal shape, among other possible shapes, and an open architecture, e.g. at least two openings and a central cavity extending therebetween, suitable for implantation between adjacent vertebral bodies.

Exemplary spinal interbody fusion cages can be used in a variety of spinal interbody fusion applications. Exemplary spinal interbody cages include an anterior lumbar interbody fusion (ALIF) spinal interbody cage, a posterior lumbar interbody fusion (PLIF) spinal interbody cage, a lateral spinal interbody cage, a direct lateral interbody fusion (DLIF) spinal interbody cage, a transforaminal lumbar interbody fusion (TLIF) spinal interbody cage, an extreme lateral interbody fusion (XLIF) spinal interbody cage, and a cervical spinal interbody cage, among others.

The spinal interbody cages can be placed, for example, in cervical spine, thoracic spine, or lumbar spine. Exemplary adjacent vertebral bodies suitable for implantation of the spinal interbody cage include adjacent vertebral bodies from among C2-T1 vertebrae, adjacent vertebral bodies from among T1-T12 vertebrae, adjacent vertebral bodies of L4-L5 vertebra, and adjacent vertebral bodies of L5-S1 vertebrae, among others.

As used herein, the term "mesh structure" means a structure comprising mesh links and having mesh openings between the mesh links. The mesh structure can have a regular structure, a non-regular structure, and/or a random structure, among other structures, based on dimensions and arrangement of the mesh links. In some examples the mesh links have uniform dimensions and are arranged in a regular pattern, e.g. as a regular grid formed by two sets of intersecting mesh links, the mesh links of the first set being arranged parallel to each other, and the mesh links of the second set being arranged perpendicularly to the mesh links of the first set. Also in some examples the mesh links can have non-uniform dimensions and/or can be arranged in other ways, e.g. non-repeating patterns and/or randomly.

Each mesh link can have a width of, for example, 100 to 2,000 µm, 250 µm to 1,000 µm, 300 µm to 500 µm, 350 µm to 450 µm, or 395 µm to 405 µm.

Similarly, each mesh link can have a mesh link depth of, for example, 100 to 2,000 µm, 250 µm to 1,000 µm, 300 µm to 500 µm, 350 µm to 450 µm, or 395 µm to 405 µm. A mesh link can have, as seen from a top view, a rectangular shape or a square shape, or alternatively can have other polygonal, curvilinear, or variable shapes.

The mesh openings are defined by the mesh links, i.e. the mesh openings correspond to openings between intersecting mesh links. The mesh openings can have a mesh opening area, i.e. an area defined by intersecting mesh links, of, for example, $(100 \times 100)$ to $(2,500 \times 2,500)$ µm$^2$, i.e. $1.0 \times 10^4$ µm$^2$ to $6.3 \times 10^6$ µm$^2$, $(150 \times 150)$ to $(1,000 \times 1,000)$ µm$^2$, i.e. $2.3 \times 10^4$ µm$^2$ to $1.0 \times 10^6$ µm$^2$, $(175 \times 175)$ to $(450 \times 450)$ µm$^2$, i.e. $3.1 \times 10^4$ µm$^2$ to $2.0 \times 10^5$ µm$^2$, $(190 \times 190)$ to $(410 \times 410)$ µm$^2$, i.e. $3.6 \times 10^4$ µm$^2$ to $1.7 \times 10^5$ µm$^2$, $(190 \times 190)$ to $(210 \times 210)$ µm$^2$, i.e. $3.6 \times 10^4$ µm$^2$ to $4.4 \times 10^4$ µm$^2$, or $(390 \times 390)$ to $(410 \times 410)$ µm$^2$, i.e. $1.5 \times 10^5$ µm$^2$ to $1.7 \times 10^5$ µm$^2$. Of note, the expression of mesh opening areas of mesh openings as squares of linear dimensions, e.g. (100 µm×100 µm), here and throughout this application, is for purposes of convenience only and is not intended to limit any mesh openings so described to square shapes or square mesh opening areas. The mesh openings can have a mesh opening depth, as defined by the mesh link depth, of, for example 100 to 2,000 µm, 250 µm to 1,000 µm, 300 µm to 500 µm, 350 µm to 450 µm, or 395 µm to 405 µm. A mesh opening can have, as seen from a top view, a square shape, a rectangular shape, a herringbone shape, a circular shape, or an oval shape, respectively, or alternatively can have other polygonal, curvilinear, or variable shapes.

As used herein, the term "pillar" means a projection that extends distally from a surface of a spinal interbody cage, e.g. from a top face, a bottom face, a top mesh structure, and/or a bottom mesh structure of the spinal interbody cage, that is not in direct physical contact with any other pillars or other parts of the spinal interbody cage other than the surface, and that is for contacting a vertebral body. Because a pillar is not in direct physical contact with any other pillars or other parts of the spinal interbody cage other than the surface, upon implantation no pillar forms a continuous phase within the resulting interface of the vertebral body and spinal interbody cage. A pillar can have a transverse area, i.e. an area of a cross-section taken relative to a vertical axis along which the pillar extends distally from the face of the implant, of, for example, (i) (100 μm×100 μm) to (2,000 μm×2,000 μm), i.e. $1.0×10^4$ μm$^2$ to $4.0×10^6$ μm$^2$, (ii) (250 μm×250 μm) to (1,000 μm×1,000 μm), i.e. $6.3×10^4$ μm$^2$ to $1.0×10^6$ μm$^2$, (iii) (300 μm×300 μm) to (500 μm×500 μm), i.e. $9×10^4$ μm$^2$ to $2.5×10^5$ μm$^2$, (iv) (350 μm×350 μm) to (450 μm×450 μm), i.e. $1.2×10^5$ μm$^2$ to $2.0×10^5$ μm$^2$, or (v) (395 μm×395 μm) to (405 μm×405 μm), i.e. $1.6×10^5$ μm$^2$. Of note, the expression of transverse areas of pillars as squares of linear dimensions, e.g. (100 μm×100 μm), here and throughout this application, is for purposes of convenience only and is not intended to limit any pillars so described to square shapes, square transverse areas, or square cross-sections. A pillar can have a pillar height, i.e. the height of the pillar from the face of the spinal interbody cage to the distal end of the pillar, of, for example, 100 to 2,500 μm, 200 to 1,000 μm, 400 to 600 μm, 450 to 550 μm, 490 to 510 μm, or 500 μm. A pillar can have a volume corresponding to the product of pillar transverse area and pillar height. A pillar can have, as seen from a top view, a square shape, a rectangular shape, a herringbone shape, a circular shape, or an oval shape, respectively, or alternatively can have other polygonal, curvilinear, or variable shapes.

As used herein, the term "slot" means the spaces between the pillars. Accordingly, the pillars define the slots. The slots can have a slot height, as defined by the pillars, of, for example, 100 to 2,500 μm, 200 to 1,000 μm, 400 to 600 μm, 450 to 550 μm, 490 to 510 μm, or 500 μm. The slots can have a slot width as measured along the shortest distance between adjacent pillars of, for example, 100 to 2,500 μm, 150 to 1,000 μm, 175 to 450 μm, 190 to 410 μm, 190 to 210 μm, or 390 to 410 μm. The slots have a volume corresponding to the volume of the space between the pillars.

As used herein, the term "pore" means a void space of less than 1,000 μm in size, i.e. having a diameter of less than 1,000 μm, on or below a surface, e.g. the surface of a spinal interbody cage, that is not a mesh opening. Pores can occur in a material naturally, e.g. based on a natural porosity of the material, or can be introduced, e.g. by chemical or physical treatment. Pores can be continuous with respect to each other, based on being interconnected with each other below a surface, or pores can be discontinuous, based on not being interconnected with each other below a surface. Pores can be sufficiently large to allow for migration and proliferation of osteoblasts and mesenchymal cells. Accordingly, for example, a porous surface is a surface that includes void spaces of less than 1,000 μm in size in the surface, whereas a non-porous surface is a surface that does not include such a void space.

As used herein, the term "interface resulting from implantation of the spinal interbody cage into bone of vertebral bodies," or more simply "interface," means the product of implantation wherein the pillars of the spinal interbody cage are contacting vertebral bodies and the slots of the spinal interbody cage are occupied, partially or completely, by bone of vertebral bodies and/or bone of bone graft. The interface includes (i) the pillars, (ii) bone that occupies the slots of the spinal interbody cage, (iii) any remaining unoccupied space in the slots, (iv) any bone that occupies any additional space between the face of the spinal interbody cage and a plane defined by the distal ends of the pillars, (v) any bone that occupies any additional space between the mesh structure of the spinal interbody cage and a plane defined by the distal ends of the pillars, not including space within the mesh openings, and (vi) any bone that occupies any pores on the face or the pillars. Accordingly, the interface boundaries are the face and mesh structure of the spinal interbody cage, the internal surfaces of any pores on the face, and the bulk bone surrounding the interface.

In some example embodiments, e.g. immediately after implanting the spinal interbody cage between adjacent vertebral bodies with at least some penetration of the pillars into bone of the vertebral bodies and/or after at least some remodeling and growth of the bone of vertebral bodies and/or bone graft to partially fill in space between the spinal interbody cage and the bone, the pillars are contacting the vertebral bodies (e.g. at distal ends of the pillars), and the slots and/or mesh openings are partially occupied by the bone. In other example embodiments, e.g. after implanting the spinal interbody cage between adjacent vertebral bodies and further after extensive remodeling and growth of the bone of vertebral bodies and/or bone of bone graft to fill in all space between the spinal interbody cage and the bone, the pillars are contacting the vertebral bodies (e.g. at distal ends and lateral surfaces of the pillars), and the slots and/or mesh openings are completely occupied by the bone of vertebral bodies and/or bone of bone graft. In other example embodiments, the pillars contact bone of vertebral bodies and/or bone of bone graft over time, based on remodeling and growth of bone of vertebral bodies and/or bone of bone graft in and around the pillars, e.g. during healing.

As used herein, the term "continuous," when used for example in reference to the bone of vertebral bodies and/or bone of bone graft of an interface, means that the bone forms a single continuous phase, extending throughout and across the interface to each boundary of the interface. As used herein, the term "discontinuous," when used for example in reference to the spinal interbody cage of an interface, means that the spinal interbody cage does not form such a single continuous phase.

Figure 14:
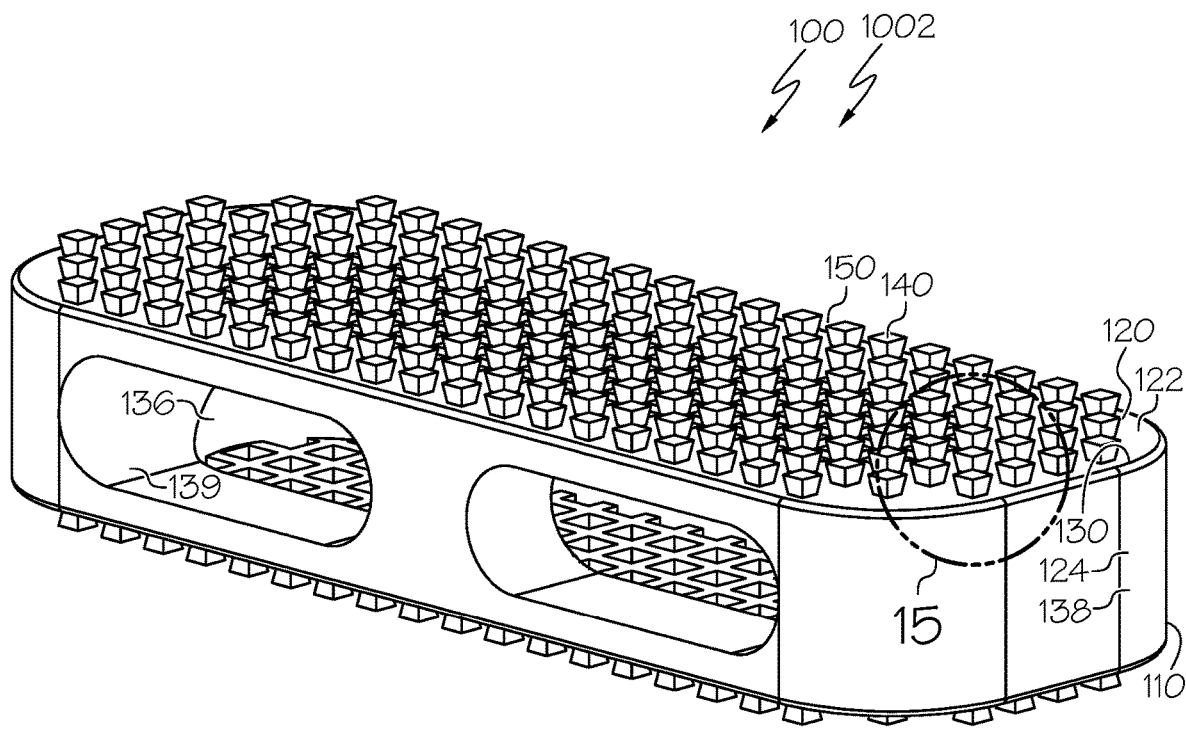
FIG. 14 is a top perspective view of an example spinal interbody cage including pillars in which the spinal interbody cage has a parallel profile and the pillars extend perpendicularly from a top face, a bottom face, a top mesh structure, and a bottom mesh structure of the spinal interbody cage and in which the pillars have transverse areas that increase distally.
Figure 15:
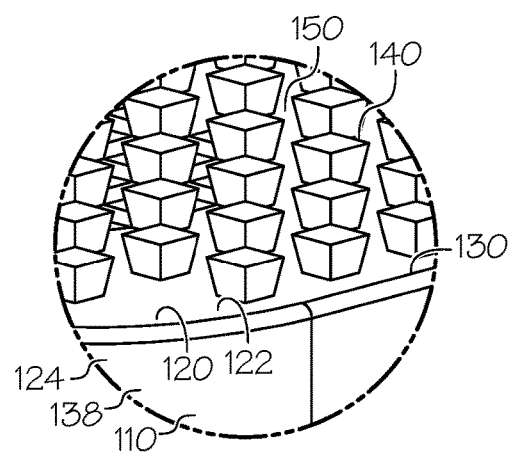
FIG. 15 is an expanded top perspective view of a portion of the spinal interbody cage of FIG. 14.
Figure 16:
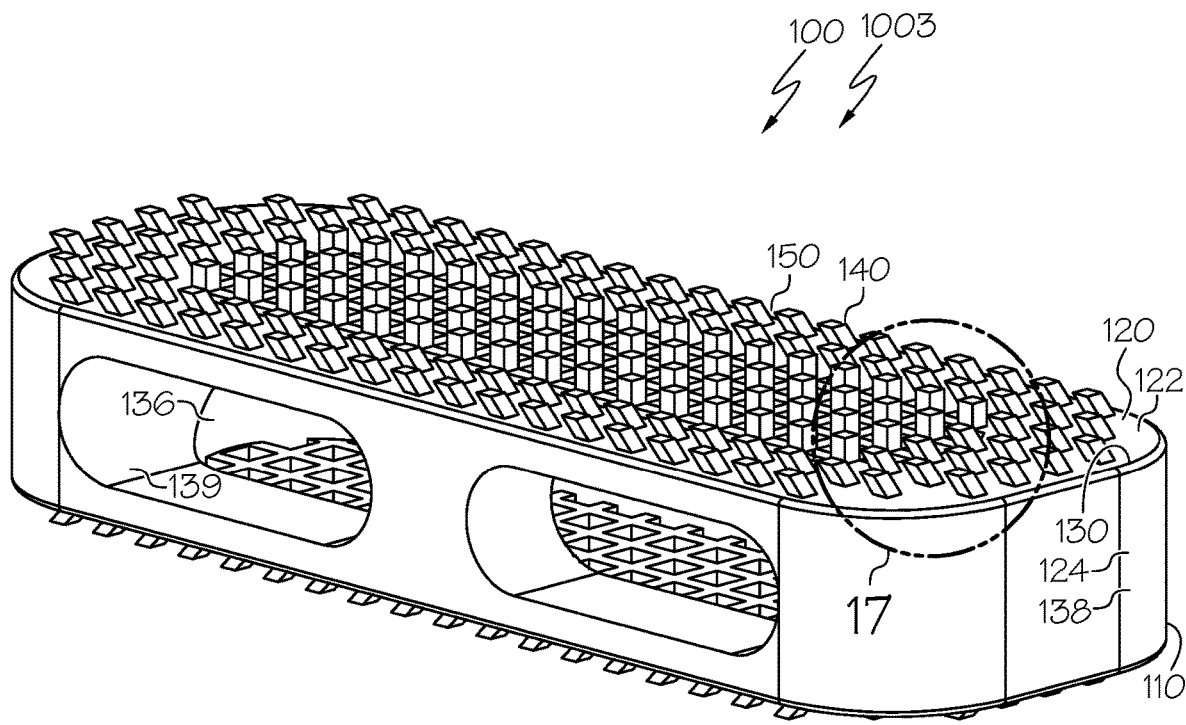
FIG. 16 is a top perspective view of an example spinal interbody cage including pillars in which the spinal interbody cage has a parallel profile and some pillars extend distally at a different angle relative to other pillars.
Figure 17:
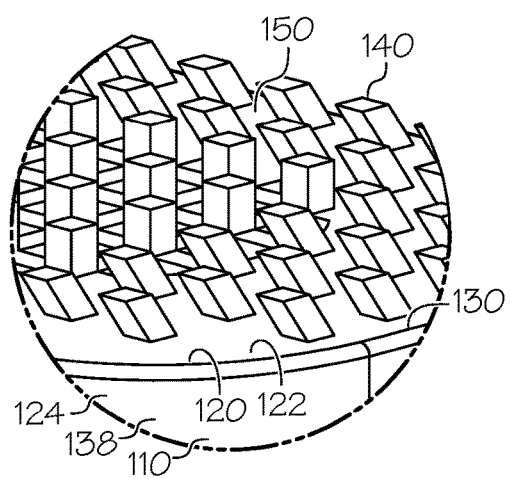
FIG. 17 is an expanded top perspective view of a portion of the spinal interbody cage of FIG. 16.
Figure 28:
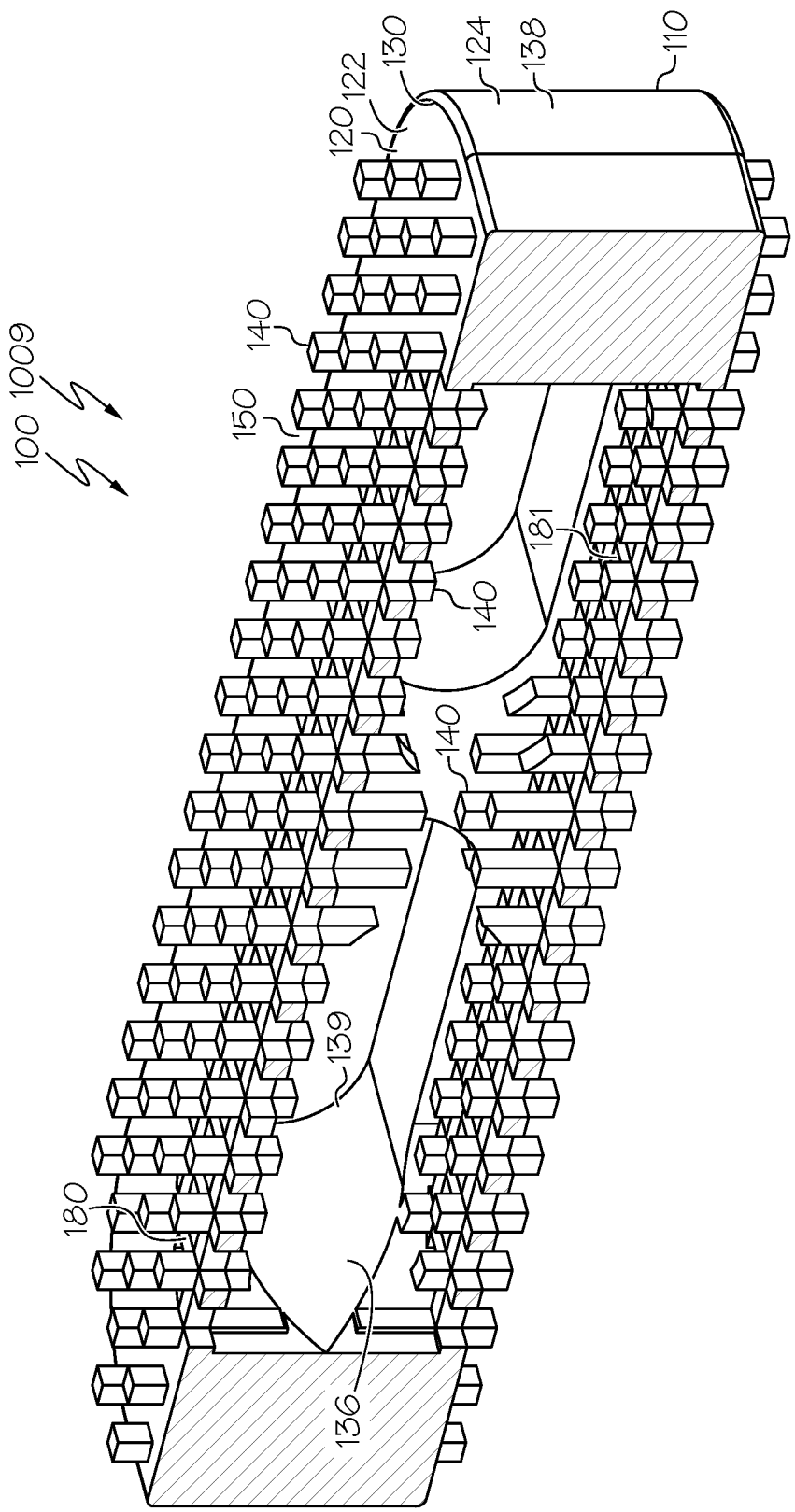
FIG. 28 is a sectional view of the spinal interbody cage of FIG. 27.
Figure 29:
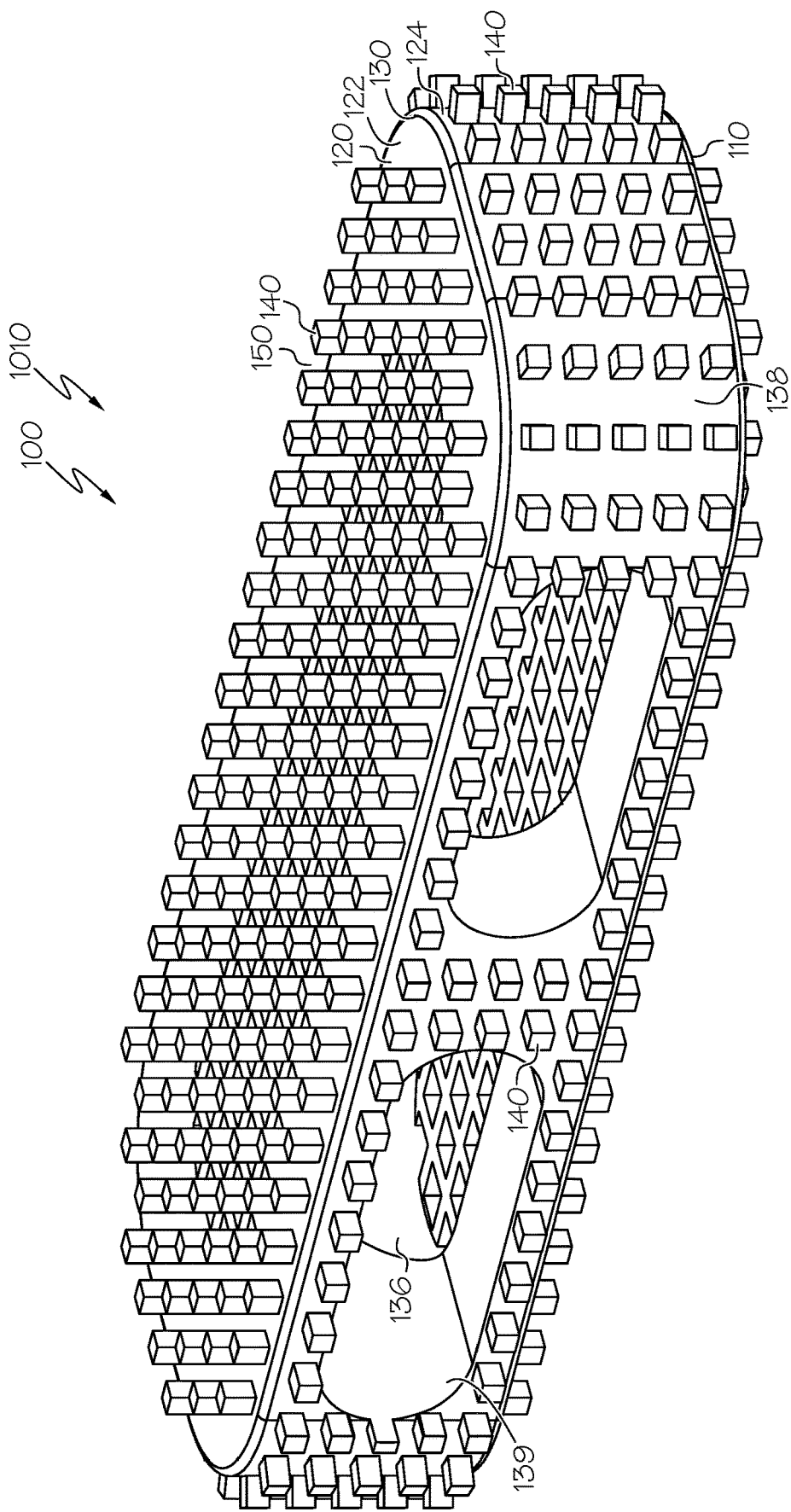
FIG. 29 is a top perspective view of an example spinal interbody cage similar to that of FIG. 1 in which the spinal interbody cage has a parallel profile and the spinal interbody cage comprises at least one lateral exterior surface comprising pillars extending from the lateral exterior surface.
Figure 30:
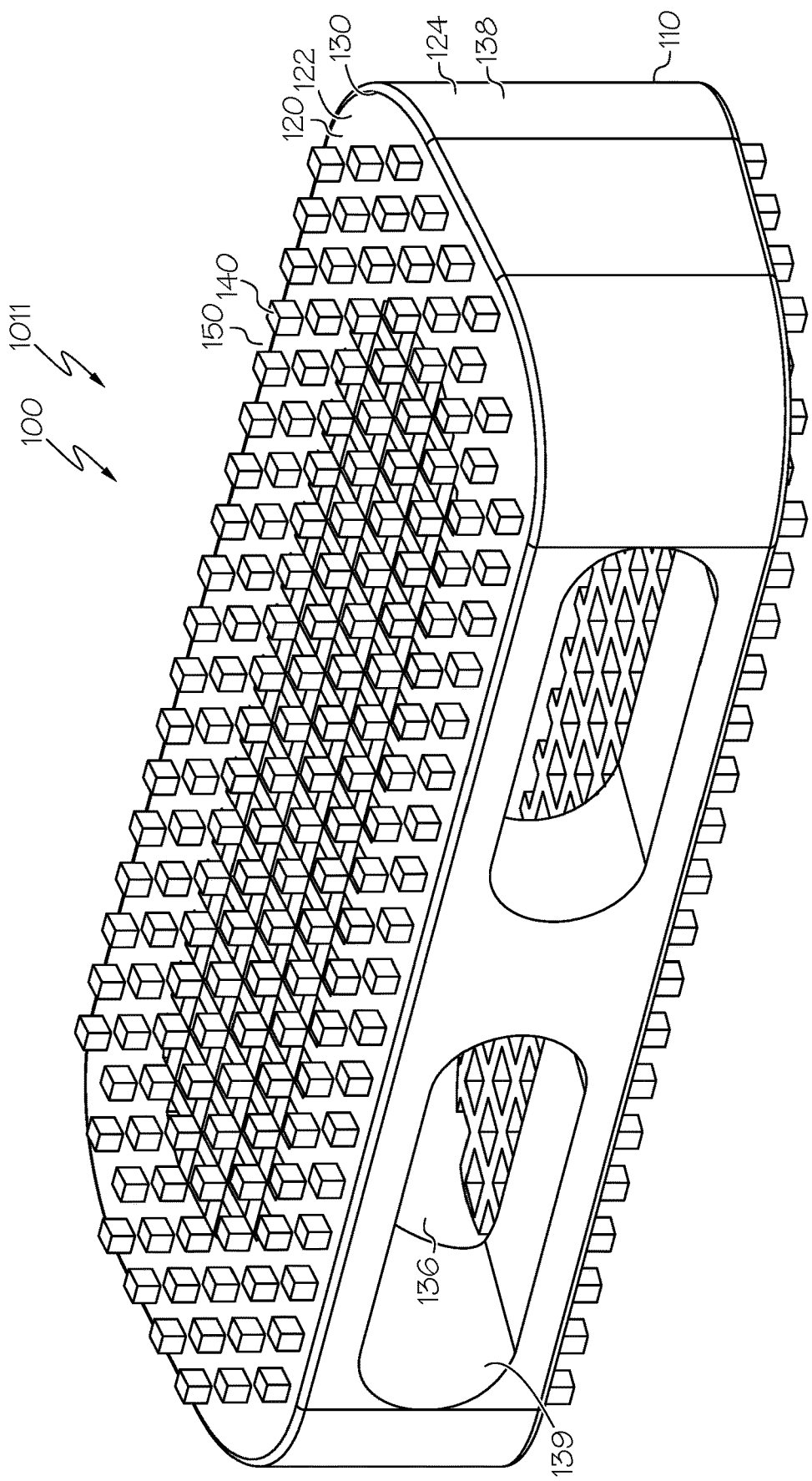
FIG. 30 is a top perspective view of an example spinal interbody cage including pillars in which the spinal interbody cage has a lordotic profile.
Figure 31:
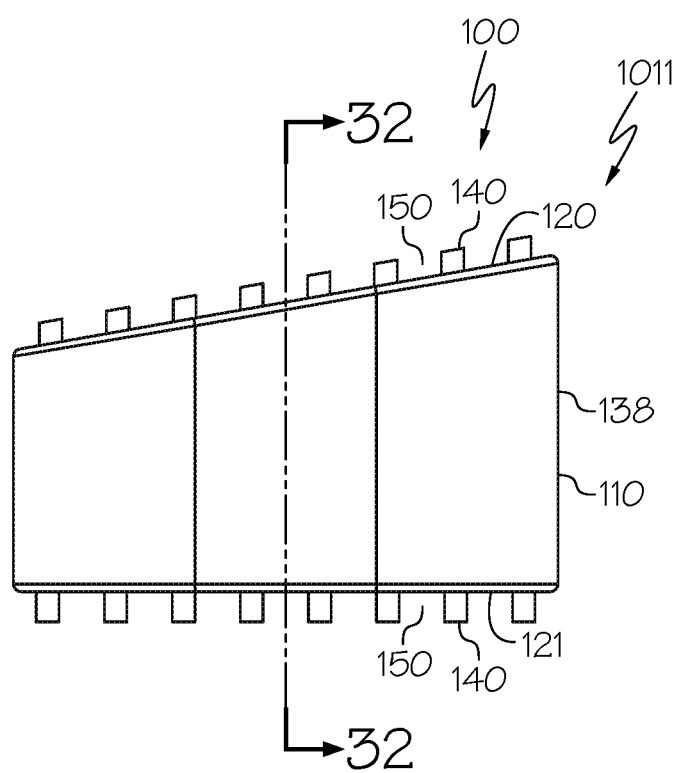
FIG. 31 is a side elevational view of the spinal interbody cage of FIG. 30.
Figure 32:
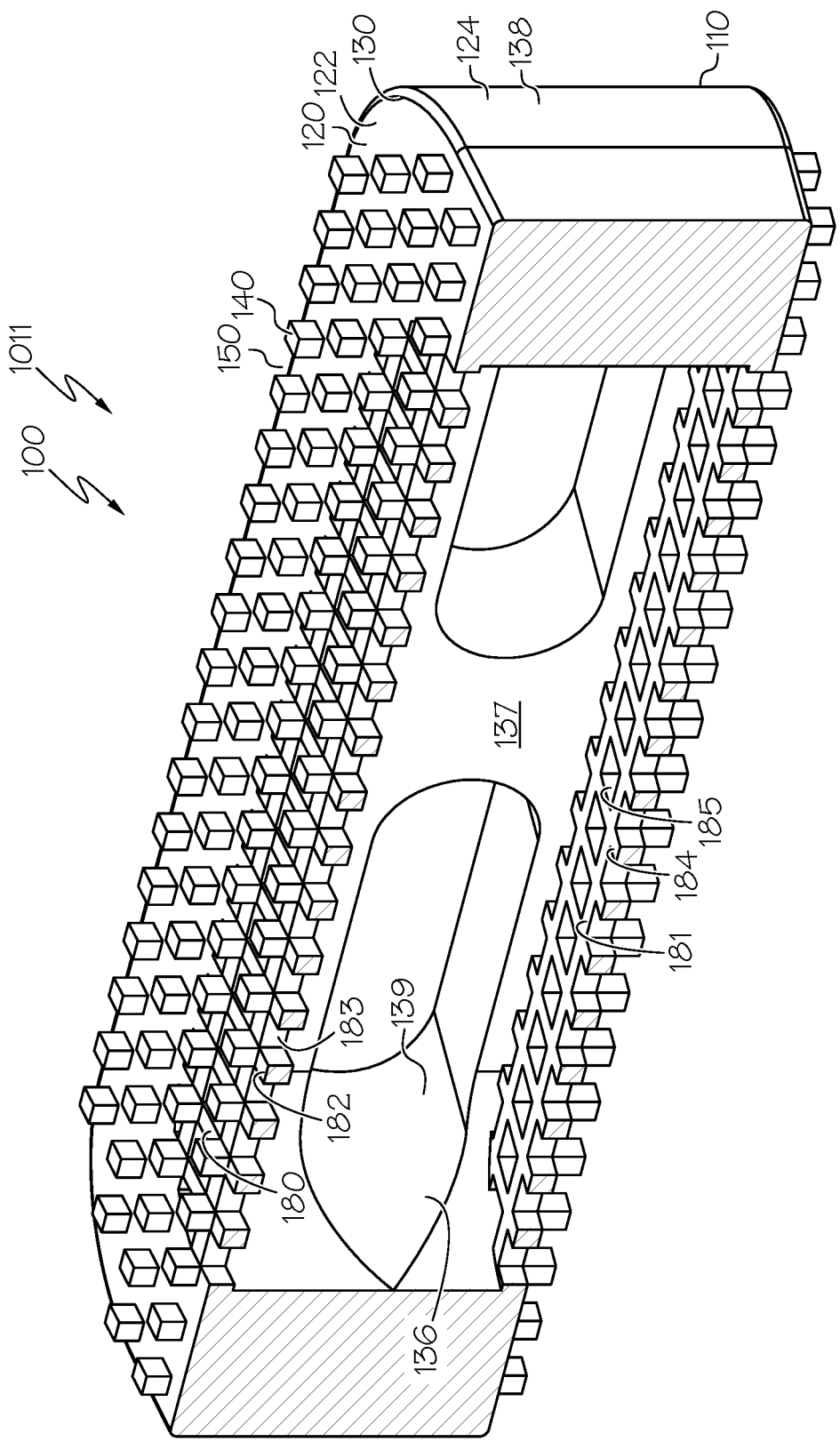
FIG. 32 is a sectional view of the spinal interbody cage of FIG. 31.
Figure 33:
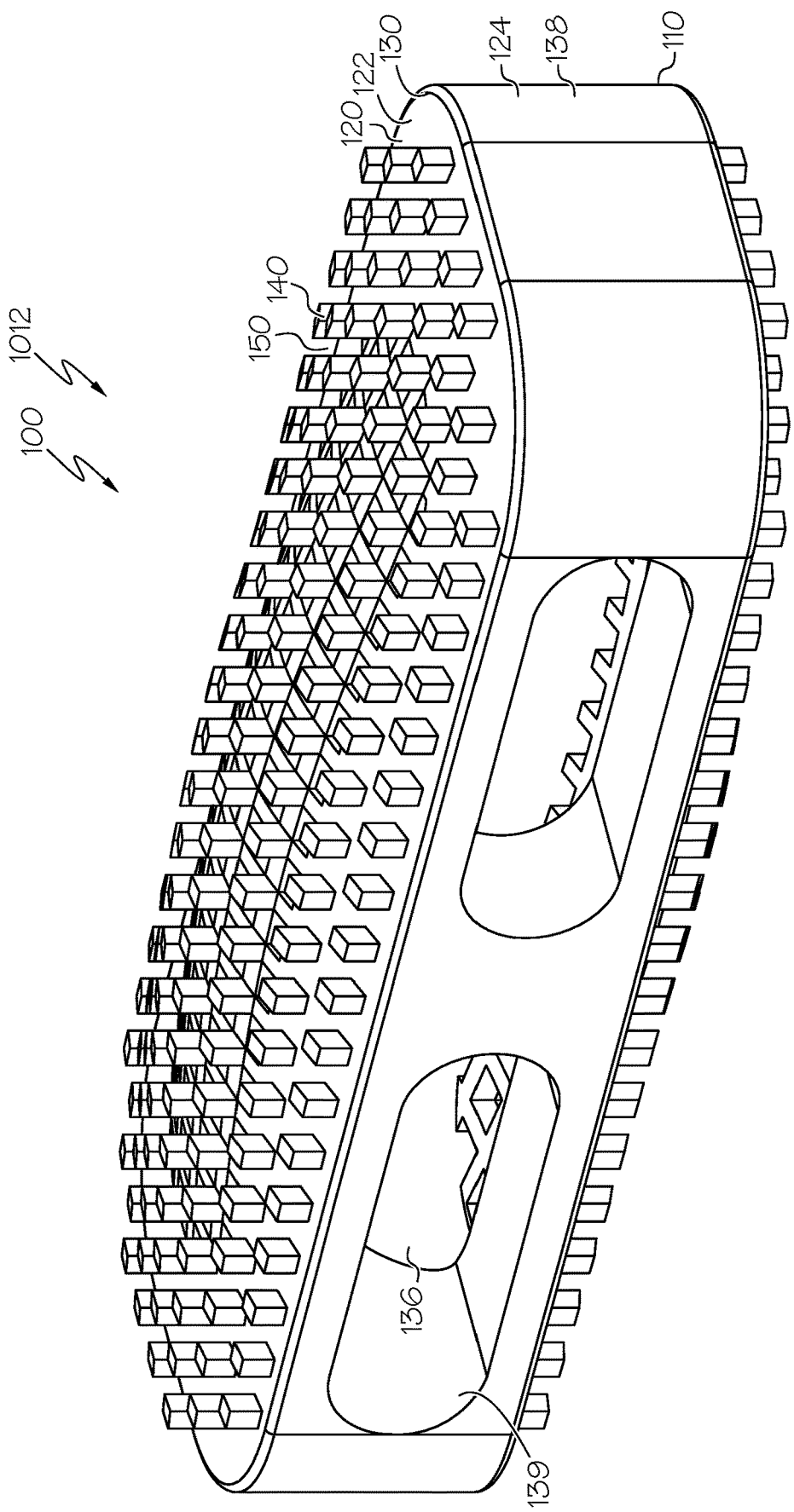
FIG. 33 is a top perspective view of an example spinal interbody cage including pillars in which the spinal interbody cage has a domed profile.
Figure 34:
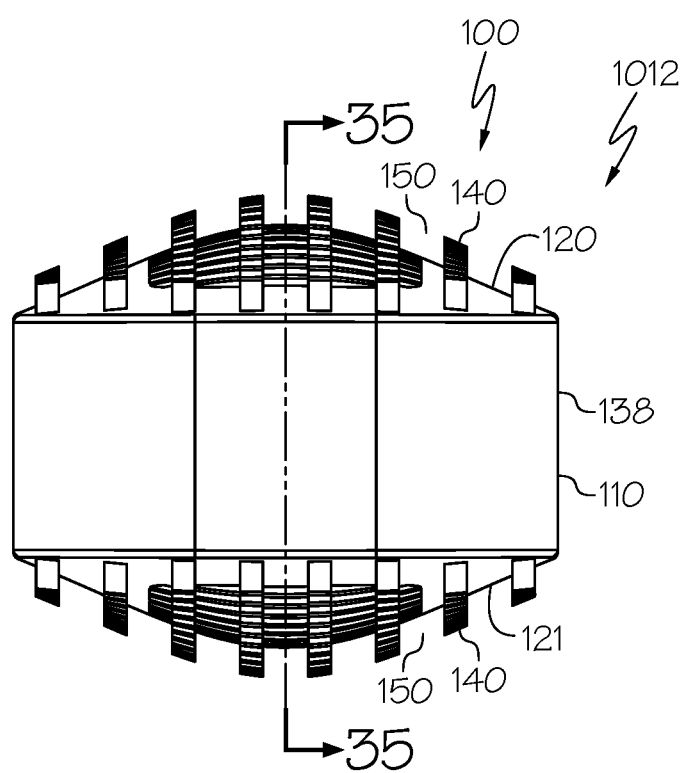
FIG. 34 is a side elevational view of the spinal interbody cage of FIG. 33.

Considering features of example spinal interbody cages in more detail, FIG. 1 provides an illustration in perspective view of an example spinal interbody cage 100, corresponding to a lateral spinal interbody cage 1001 that has a parallel profile. Additional views of the lateral spinal interbody cage 1001 are shown in FIGS. 8-13. Similarly, FIG. 14, FIG. 16, FIG. 18, FIG. 20, and FIG. 29 provide illustrations in perspective view of other example spinal interbody cages 100 corresponding to lateral spinal interbody cages 1002, 1003, 1004, 1005, and 1010, respectively, that also have parallel profiles. Additional views of the lateral spinal interbody cages 1002, 1003, and 1004 are shown in FIG. 15, FIG. 17, and FIG. 19, respectively. FIG. 21, FIG. 23, FIG. 25, and FIG. 27 provide illustrations in side elevational view of other example spinal interbody cages 100 corresponding to lateral spinal interbody cages 1006, 1007, 1008, and 1009, respectively, that also have parallel profiles. Additional views of the lateral spinal interbody cages 1006, 1007, 1008, and 1009 are shown in FIG. 22, FIG. 24, FIG. 26, and FIG. 28, respectively. FIG. 30 provides an illustration in perspective view of an example spinal interbody cage 100, corresponding to a lateral spinal interbody cage 1011 that has a lordotic profile. Additional views of the lateral spinal interbody cage 1011 are shown in FIG. 31 and FIG. 32. FIG. 33 provides an illustration in perspective view of an example spinal interbody cage 100, corresponding to a lateral spinal interbody cage 1012 that has a domed profile. Additional views of the lateral spinal interbody cage 1012 are shown in FIG. 34 and FIG. 35.

The spinal interbody cage 100 can be made from a material having a Young's modulus of elasticity, i.e. a tensile modulus of elasticity, of at least 3 GPa, as measured at 21° C. The spinal interbody cage 100 can be made, for example, from one or more materials such as implantable-grade polyaryletherketone that is essentially unfilled (such as implantable-grade polyetheretherketone or implantable-grade polyetherketoneketone), titanium, stainless steel, cobalt-chromium alloy, titanium alloy (such as Ti-6Al-4V titanium alloy or Ti-6Al-7Nb titanium alloy), ceramic material (such as silicon nitride (Si3N4)), or implantable-grade composite material (such as implantable-grade polyaryletherketone with filler, implantable-grade polyetheretherketone with filler, implantable-grade polyetheretherketone with carbon fiber, or implantable-grade polyetheretherketone with hydroxyapatite). Specific examples include (i) implantable-grade polyetheretherketone that is essentially unfilled, which has a Young's modulus of approximately 4 GPa, (ii) implantable-grade polyetheretherketone with filler, e.g. carbon-fiber-reinforced implantable-grade polyetheretherketone, which has a Young's modulus of elasticity of at least 18 GPa, (iii) titanium, which has a Young's modulus of elasticity of approximately 110 GPa, (iv) stainless steel, which has a Young's modulus of elasticity of approximately 200 GPa, (v) cobalt-chromium alloy, which has a Young's modulus of elasticity of greater than 200 GPa, or (vi) titanium alloy, which has a Young's modulus of elasticity of approximately 105-120 GPa, all as measured at 21° C. The spinal interbody cage 100 also can be made, for example, from one or more hard tissues such as a hard tissue obtained from a human or animal (such as autologous hard tissue, allogenic hard tissue, or xenogeneic hard tissue), human cartilage, animal cartilage, human bone, animal bone, cadaver bone, or cortical allograft. Such hard tissues obtained from a human or animal can have a Young's modulus of elasticity of, e.g. 4 to 18 GPa. Such hard tissues obtained from a human or animal can also be treated, in advance of implantation, to decrease or eliminate the capacity of the hard tissue to elicit an immune response in an individual upon implantation into the individual. The spinal interbody cage 100 also can be made, for example, from one or more materials such as resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic. The spinal interbody cage 100 also can be made from further combinations of the above-noted materials and/or hard tissues. Accordingly, the spinal interbody cage 100 has a Young's modulus of elasticity of at least 3 GPa, for example 18 to 230 GPa, 18 to 25 GPa, 100 to 110 GPa, 190 to 210 GPa, 200 to 230 GPa, 105 to 120 GPa, or 4 to 18 GPa.

Figure 8:
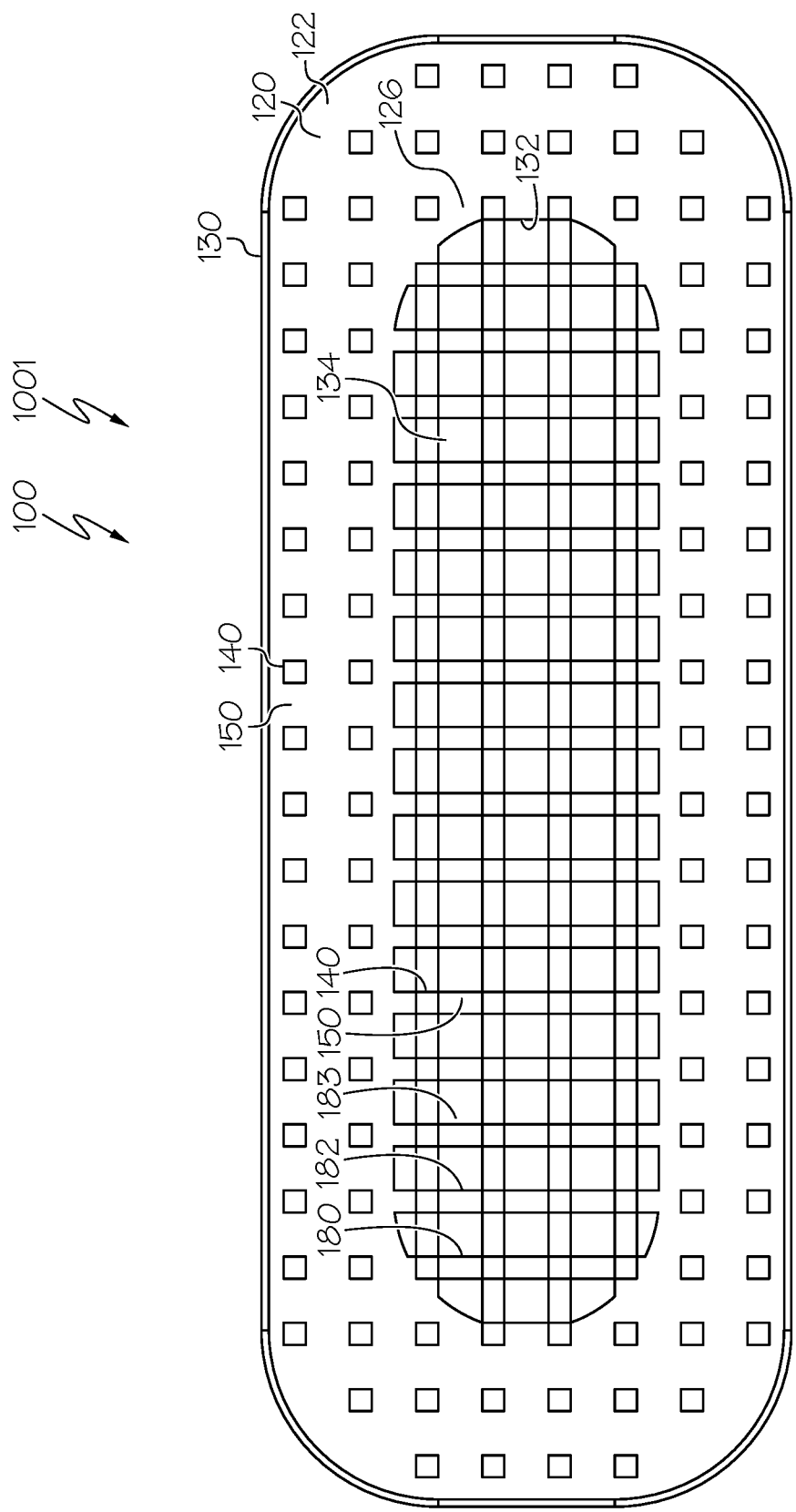
FIG. 8 is a top plan view of the spinal interbody cage of FIG. 1.

As shown in FIG. 1, FIG. 8, and FIG. 9, the spinal interbody cage 100 includes a bulk interbody cage 110, a top face 120, a bottom face 121, a top mesh structure 180, a bottom mesh structure 181, pillars 140, and slots 150.

Considering the bulk interbody cage 110 in more detail, as shown in FIG. 1, FIG. 8, and FIGS. 11-13, the bulk interbody cage 110 forms the core of the spinal interbody cage 100 and can have a generally cuboidal shape, although other three-dimensional shapes may be used in further examples. The bulk interbody cage 110 includes at least two openings, e.g. a top central opening 134 and a bottom central opening 135, as discussed below, and a central cavity 136 extending therebetween. The bulk interbody cage 110 can be made from one or more of the materials or hard tissues noted above with respect to the spinal interbody cage 100, e.g. one or more materials such as implantable-grade polyaryletherketone that is essentially unfilled (such as implantable-grade polyetheretherketone or implantable-grade polyetherketoneketone), titanium, stainless steel, cobalt-chromium alloy, titanium alloy (such as Ti-6Al-4V titanium alloy or Ti-6Al-7Nb titanium alloy), ceramic material (such as silicon nitride (Si3N4)), or implantable-grade composite material (such as implantable-grade polyaryletherketone with filler, implantable-grade polyetheretherketone with filler, implantable-grade polyetheretherketone with carbon fiber, or implantable-grade polyetheretherketone with hydroxyapatite), or e.g. one or more hard tissues such as a hard tissue obtained from a human or animal (such as autologous hard tissue, allogenic hard tissue, or xenogeneic hard tissue), human cartilage, animal cartilage, human bone, animal bone, cadaver bone, or cortical allograft, or e.g. one or more materials such as resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic.

The bulk interbody cage 110 can be porous or non-porous. For example, the bulk interbody cage 110 can include one or more surfaces that are porous, and/or can be made from one or more materials that are porous. Such porous surfaces can include pores having diameters of, e.g. 1 to 900 µm, 100 to 800 µm, or 200 to 600 µm. Also for example, the bulk interbody cage 110 can include only surfaces that are non-porous, and/or can be made only from one or more materials that are non-porous.

Figure 12:
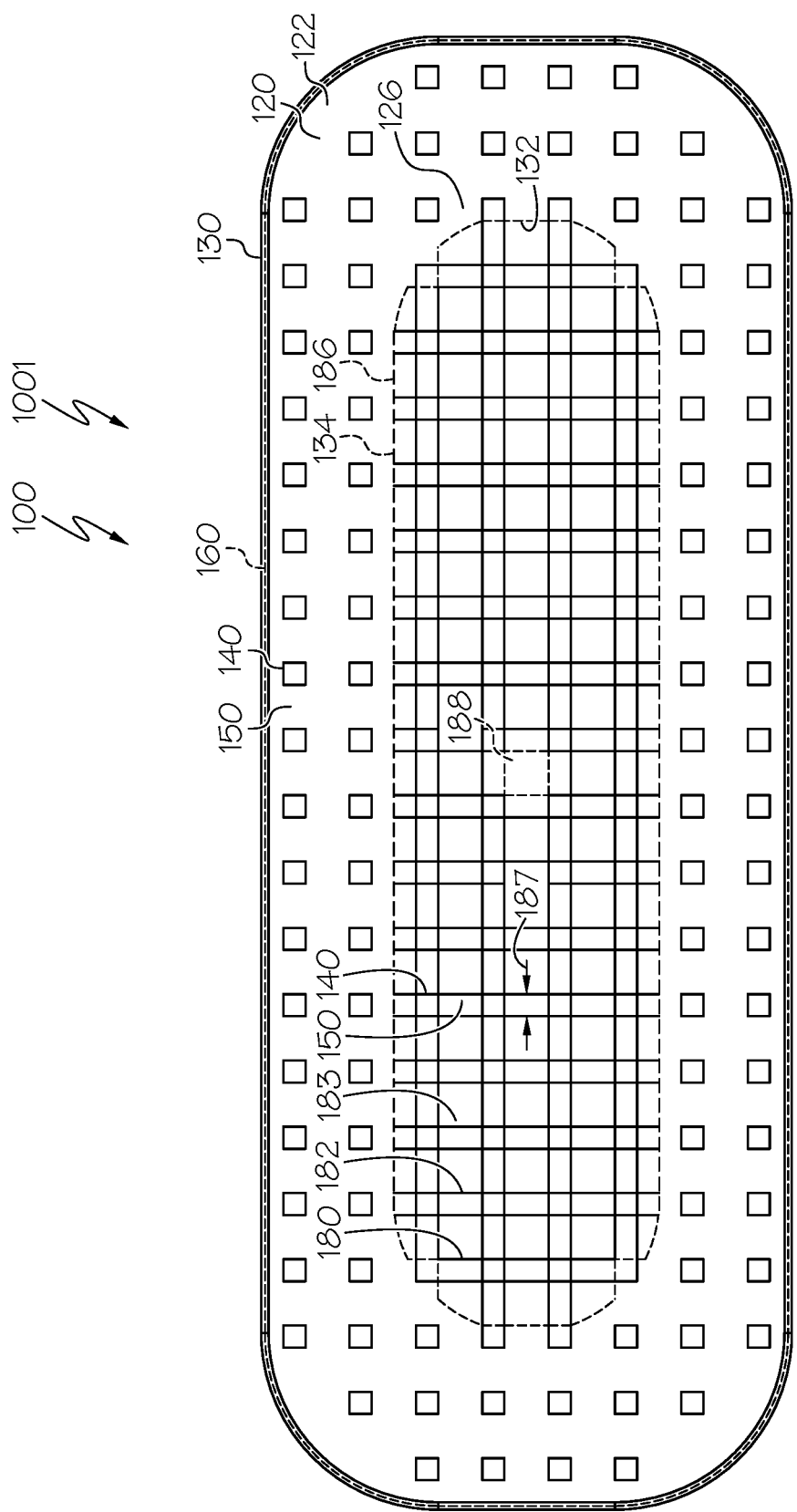
FIG. 12 is another top plan view of the spinal interbody cage of FIG. 1.

Considering now the top face 120 in more detail, as shown in FIG. 1, FIG. 8, and FIG. 12, the top face 120 of the spinal interbody cage 100 is an exterior surface of the bulk interbody cage 110, having a top central opening 134. As shown in FIG. 12, the top face 120 has a total area 160, not including an area of the top central opening 134. As shown in FIG. 1, the top face 120 can be flat, i.e. have a flat contour, or can have curvilinear, angular, and/or irregular contours. As shown in FIG. 12, the top face 120 can be defined by an outer edge 130 and an inner edge 132. The outer edge 130 and the pillars 140 closest to the outer edge 130 can define an outer peripheral border 122 of the top face 120. Likewise, the inner edge 132 and the pillars 140 closest to the inner edge 132 can define an inner peripheral border 126 of the top face 120. As shown in FIG. 1, the outer edge 130 can define an intersection between the top face 120 and one or more adjacent faces 124 of the spinal interbody cage 100. The top face 120 and the one or more adjacent faces 124 may intersect at the outer edge 130 at a right angle, although the top face 120 and the one or more adjacent faces 124 may also intersect at other angles, e.g. acute angles, obtuse angles, or varying angles. The outer edge 130 can be sharp, although other rounded, angular, smooth, and/or irregular edges may be used in further examples. The top face 120 can be porous, e.g. including pores having diameters of, e.g. 1 to 900 µm, 100 to 800 µm, or 200 to 600 µm, or the top face 120 can be non-porous.

The bottom face 121 is a bottom exterior surface, having a bottom central opening 135. The bottom face 121 has a total area 161, not including an area of the bottom central opening 135. The bottom face 121 can have a similar layout as the top face 120, as described above and as follows, including an outer edge 131, and inner edge 133, an outer peripheral border 123, and an inner peripheral border 127, like the corresponding ones of the top face 120, among other similarities.

Considering the top mesh structure 180 in more detail, as shown in FIG. 1, FIG. 8, and FIG. 12, the top mesh structure 180 extends from the bulk interbody cage 110 across the top central opening 134, comprises top mesh links 182, and has top mesh openings 183 between the top mesh links 182. As shown in FIG. 1 and FIG. 12, by extending from the bulk interbody cage 110 across the top central opening 134, the top mesh structure 180 partially covers the top central opening 134, i.e. the top central opening 134 remains open to the extent that the top mesh openings 183 of the top mesh structure 180 are open. As shown in FIG. 12, the top mesh structure 180 has a total area 186, defined by the inner edge 132 of the top face 120. The top mesh openings 183 are defined by the top mesh links 182, i.e. the top mesh openings 183 correspond to openings between intersecting top mesh links 182. The top mesh structure 180 can be made from one or more of the materials noted above with respect to the spinal interbody cage 100.

The top mesh structure 180 can have a regular structure, a non-regular structure, and/or a random structure, among other structures, based on dimensions and arrangement of the top mesh links 182. Thus, in some examples the top mesh links 182 have uniform dimensions and are arranged in a regular pattern, e.g. as a regular grid formed by two sets of intersecting top mesh links 182, the top mesh links 182 of the first set being arranged parallel to each other, and the top mesh links 182 of the second set being arranged perpendicularly to the top mesh links 182 of the first set. Also in some examples the top mesh links 182 can have non-uniform dimensions and/or can be arranged in other ways, e.g. non-repeating patterns and/or randomly.

With respect to dimensions of the top mesh links 182, as shown in FIG. 12, each top mesh link 182 can have a top mesh link width 187, i.e. a distance across a top mesh link 182, of, for example, (i) 100 to 2,000 µm, (ii) 250 µm to 1,000 µm, (iii) 300 µm to 500 µm, (iv) 350 µm to 450 µm, or (v) 395 µm to 405 µm. Similarly, each top mesh link 182 can have a top mesh link depth of, for example, 100 to 2,000 µm, 250 µm to 1,000 µm, 300 µm to 500 µm, 350 µm to 450 µm, or 395 µm to 405 µm. A top mesh link 182 can have, as seen from a top view, a rectangular shape or a square shape, or alternatively can have other polygonal, curvilinear, or variable shapes.

With respect to dimensions of the top mesh openings 183, as shown in FIG. 12, each top mesh opening 183 can have a top mesh opening area 188, i.e. an area defined by intersecting top mesh links 182, of, for example (i) (100× 100) to (2,500×2,500) µm$^2$, i.e. $1.0\times10^4$ µm$^2$ to $6.3\times10^6$ µm$^2$, (ii) (150×150) to (1,000×1,000) µm$^2$, i.e. $2.3\times10^4$ µm$^2$ to $1.0\times10^6$ µm$^2$, (iii) (175×175) to (450×450) µm$^2$, i.e. $3.1\times10^4$ µm$^2$ to $2.0\times10^5$ µm$^2$, (iv) (190×190) to (410×410) µm$^2$, i.e. $3.6\times10^4$ µm$^2$ to $1.7\times10^5$ µm$^2$, (v)(190×190) to (210×210) µm$^2$, i.e. $3.6\times10^4$ µm$^2$ to $4.4\times10^4$ µm$^2$, or (vi) (390×390) to (410×410) µm$^2$, i.e. $1.5\times10^5$ µm$^2$ to $1.7\times10^5$ µm$^2$. The top mesh openings 183 can have a top mesh opening depth, as defined by the top mesh link depth, of, for example 100 to 2,000 µm, 250 µm to 1,000 µm, 300 µm to 500 µm, 350 µm to 450 µm, or 395 µm to 405 µm. A top mesh opening 183 can have, as seen from a top view, a square shape, a rectangular shape, a herringbone shape, a circular shape, or an oval shape, respectively, or alternatively can have other polygonal, curvilinear, or variable shapes.

Like the bulk interbody cage 110, the top mesh structure 180 can be porous or non-porous. For example, the top mesh structure 180 can include one or more surfaces that are porous, and/or can be made from one or more materials that are porous. Such porous surfaces can include pores having diameters of, e.g. 1 to 900 µm, 100 to 800 µm, or 200 to 600 µm. Also for example, the top mesh structure 180 can include only surfaces that are non-porous, and/or can be made only from one or more materials that are non-porous.

Figure 13:
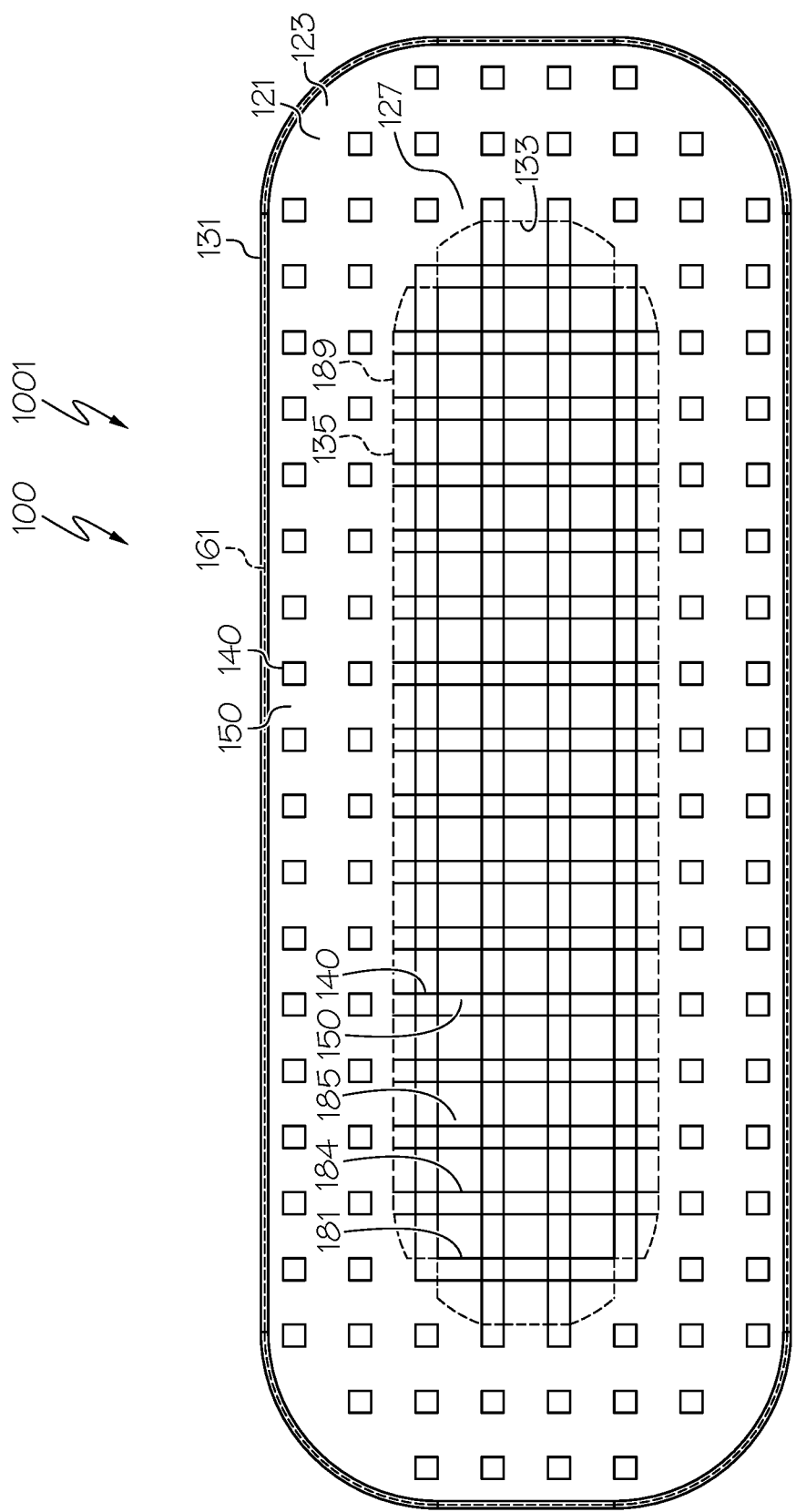
FIG. 13 is a bottom plan view of the spinal interbody cage of FIG. 1.

As shown in FIG. 1 and FIG. 13, the bottom mesh structure 181 extends from the bulk interbody cage 110 across the bottom central opening 135, comprises bottom mesh links 184, and has bottom mesh openings 185 between the bottom mesh links 184. Similarly as for the top mesh structure 180, by extending from the bulk interbody cage 110 across the bottom central opening 135, the bottom mesh structure 181 partially covers the bottom central opening 135. As shown in FIG. 13, the bottom mesh structure 181 has a total area 189, defined by the inner edge 133 of the bottom face 121. The bottom mesh openings 185 are defined by the bottom mesh links 184, i.e. the bottom mesh openings 185 correspond to openings between intersecting bottom mesh links 184. The bottom mesh structure 181 can be made from one or more of the materials noted above with respect to the spinal interbody cage 100. The bottom mesh structure 181 can have a similar structure as the top mesh structure 180, as described above and as follows, e.g. the bottom mesh structure 181 can have a regular structure, a non-regular structure, and/or a random structure, among other structures, and the bottom mesh structure 181 can be porous or non-porous. The bottom mesh links 184 and bottom mesh openings 185 can have dimensions as described for the top mesh links 182 and the top mesh openings 183, respectively.

Considering now the pillars 140 in more detail, the pillars 140 are for contacting vertebral bodies. The vertebral bodies can also be selected, for example, from the group consisting of adjacent vertebral bodies from among C2-T1 vertebrae, adjacent vertebral bodies from among T1-T12 vertebrae, adjacent vertebral bodies of L4-L5 vertebra, and adjacent vertebral bodies of L5-S1 vertebrae. In some examples, the pillars 140 may contact a vertebral body immediately upon implantation, e.g. based on extending distally from a top face 120 or a bottom face 121 of the spinal interbody cage 100. In some examples, some pillars 140 may contact a vertebral body over time after implantation, e.g. based on remodeling and growth of bone of vertebral bodies and/or bone of bone graft to come in contact with pillars 140.

Figure 3:
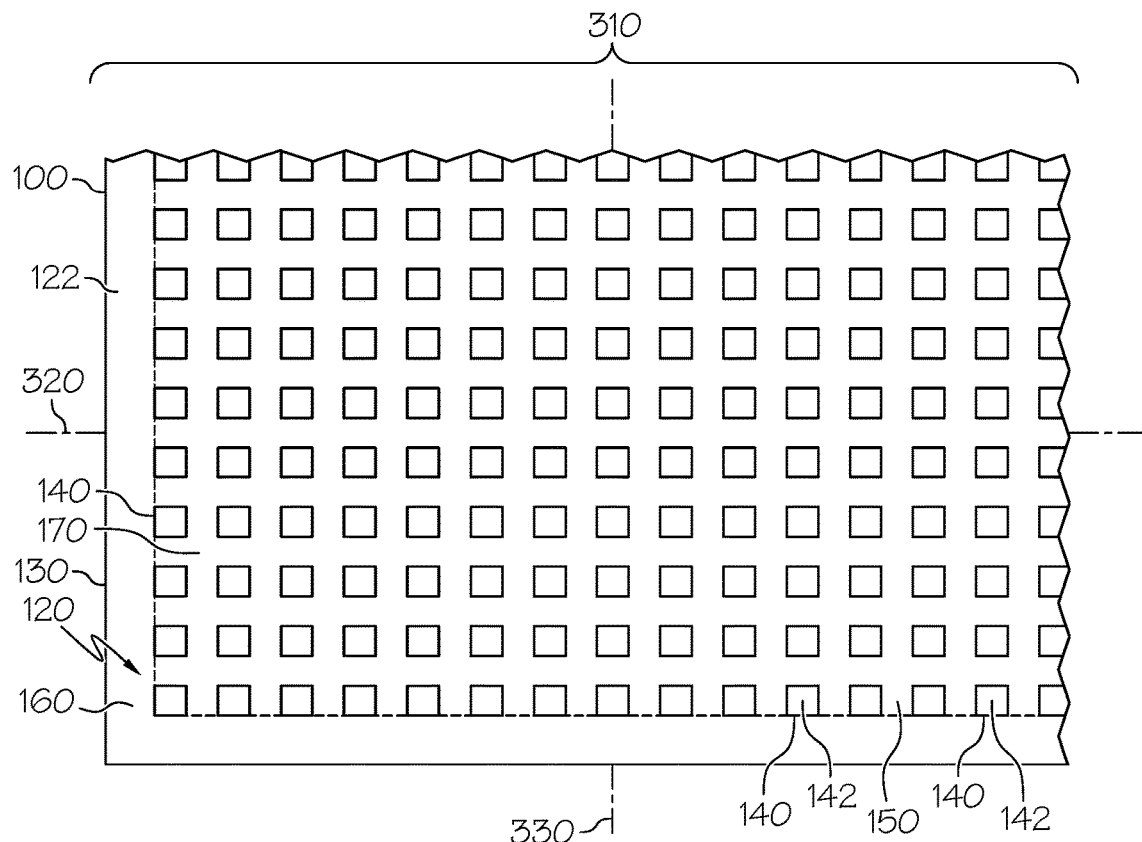
FIG. 3 is a schematic top plan view of a portion of an example spinal interbody cage including pillars.

As shown in FIG. 3 and FIG. 8, the pillars 140 are distributed on the top face 120 of the spinal interbody cage 100, across an area 170 of the top face 120 of at least 25 mm$^2$. For example, the pillars 140 can be distributed in a regular pattern 310 on the top face 120 of the spinal interbody cage 100, across the area 170 of the top face 120. In this regard, the pillars 140 can be distributed in even rows along a horizontal axis 320 and a vertical axis 330 of the top face 120, and can be distributed along a given row uniformly with respect to the distances between the centers 142 of the pillars 140 in the row. Also for example, the pillars 140 can also be distributed in other regular patterns, e.g. the pillars 140 can be distributed in rows that are even with respect to the horizontal axis 320 but not the vertical axis 330, or vice versa, the pillars 140 in one row may be offset from the pillars 140 in adjacent rows, the pillars 140 may be arranged in a spiral pattern, etc. Also for example, the pillars 140 can be distributed on the top face 120 of the spinal interbody cage 100 in irregular patterns or randomly. For example, the pillars 140 can be distributed on the top face 120 of the spinal interbody cage 100 such that the pillars 140 are packed more densely on one area of the top face 120 and less densely on another area of the top face 120.

The pillars 140 also are distributed on the bottom face 121, across an area of at least 25 mm², of the bottom face 121. The pillars 140 can be distributed on the bottom face 121 similarly as on the top face 120, as described above and as follows.

As shown in FIG. 8, the pillars 140 also are distributed on the top mesh structure 180 of the spinal interbody cage 100, across an area of the top mesh structure 180 of at least 25 mm². For example, similarly as for the pillars 140 as distributed on the top face 120, the pillars 140 can be distributed on the top mesh structure 180 in a regular pattern 310, e.g. in even rows along a horizontal axis and a vertical axis of the top mesh structure 180, and can be distributed along a given row uniformly with respect to the distances between the centers 142 of the pillars 140 in the row. In some of these examples, the pillars 140 are distributed on the top mesh structure 180 in a regular pattern based on extending from the top mesh structure 180 at intersections of top mesh links 182. Also for example, the pillars 140 can also be distributed in other regular patterns, e.g. the pillars 140 can be distributed in rows that are even with respect to the horizontal axis but not the vertical axis, or vice versa, the pillars 140 in one row may be offset from the pillars 140 in adjacent rows, etc. Also for example, the pillars 140 can be distributed on the top mesh structure 180 of the spinal interbody cage 100 in irregular patterns or randomly. For example, the pillars 140 can be distributed on the top mesh structure 180 of the spinal interbody cage 100 such that the pillars 140 are packed more densely on one area of the top mesh structure 180 and less densely on another area of the top mesh structure 180.

The pillars 140 also are distributed on the bottom mesh structure 181, across an area of at least 25 mm², of the bottom mesh structure 181. The pillars 140 can be distributed on the bottom mesh structure 181 similarly as on the top mesh structure 180, as described above and as follows.

In some examples, the pillars 140 can be distributed on the top face 120 of the spinal interbody cage 100 such that none of the pillars 140 are located at an outer edge 130 and/or an inner edge 132, i.e. the face 120 can have an outer peripheral border 122 and an inner peripheral border 126 that are not occupied by any pillars 140, resulting in the area 170 of the top face 120 across which the pillars 140 are distributed being less than the total area 160 of the top face 120. Alternatively, in some examples the pillars 140 can be distributed on the top face 120 of the spinal interbody cage 100 such that at least some of the pillars 140 are located at an outer edge 130 or an inner edge 132, e.g. the area 170 of the top face 120 across which the pillars 140 are distributed can be equal to the total area 160 of the top face 120. The same applies regarding the pillars 140 distributed on the bottom face 121, with respect to an outer edge 131 and an inner edge 133 of the bottom face 121. The same also applies regarding the pillars 140 distributed on the top mesh structure 180, with respect to the inner edge 132 of the top face 120, and regarding the pillars 140 distributed on the bottom mesh structure 181, with respect to the inner edge 133 of the bottom face 121.

Figure 4:
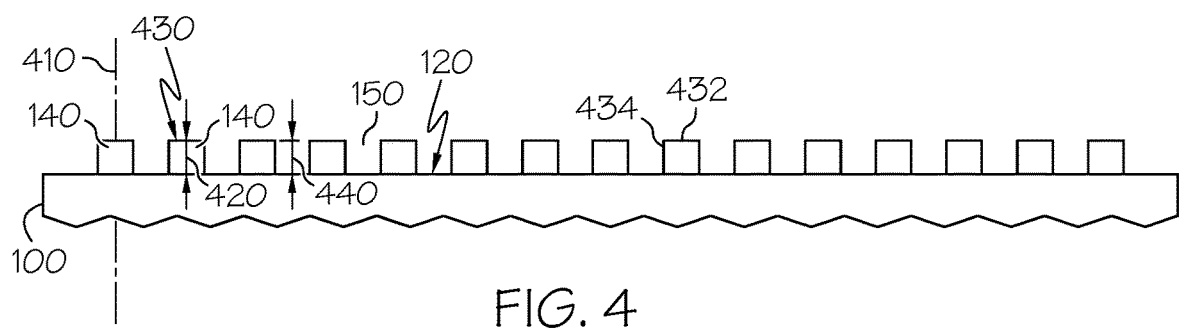
FIG. 4 is a schematic side elevational view of a portion of an example spinal interbody cage including pillars.

As shown in FIG. 4, the pillars 140 extend distally from the top face 120 of the spinal interbody cage 100. For example, the pillars 140 can extend distally along a vertical axis 410 from the top face 120 of the spinal interbody cage 100. As shown, the pillars 140 can extend in a uniform direction, i.e. all pillars 140 can extend distally at the same angle with respect to the top face 120 and in the same direction. Also for example, some pillars 140 may extend distally at a different angle and/or in a different direction relative to other pillars 140, for example for a spinal interbody cage 100 for which the top face 120 is not flat. As also shown, the pillars 140 can be perpendicular to the top face 120, e.g. extending perpendicularly from the top face 120. Also for example, the pillars 140 can extend from the top face 120 at other angles and/or varying angles. The same applies regarding the pillars 140 extending distally from the bottom face 121, the top mesh structure 180, and the bottom mesh structure 181. In some examples, a plurality of pillars 140 are perpendicular to the top face 120, a plurality of the pillars 140 are perpendicular to the bottom face 121, a plurality of the pillars 140 are perpendicular to the top mesh structure 180, and a plurality of the pillars 140 are perpendicular to the bottom mesh structure 181. For example, as shown in FIG. 1 with respect to the lateral spinal interbody cage 1001, in some examples each pillar 140 extending from the top face 120, the bottom face 121, the top mesh structure 180, and the bottom mesh structure 181 are perpendicular to the top face 120, the bottom face 121, the top mesh structure 180, and the bottom mesh structure 181, respectively. Also for example, as shown in FIG. 16 with respect to the lateral spinal interbody cage 1003, in some examples some of the pillars 140 extending from the top face 120, the bottom face 121, the top mesh structure 180, and the bottom mesh structure 181 are perpendicular to the top face 120, the bottom face 121, the top mesh structure 180, and the bottom mesh structure 181, respectively, and others of the pillars 140 extending from the top face 120, the bottom face 121, the top mesh structure 180, and the bottom mesh structure 181 are not.

Figure 2:
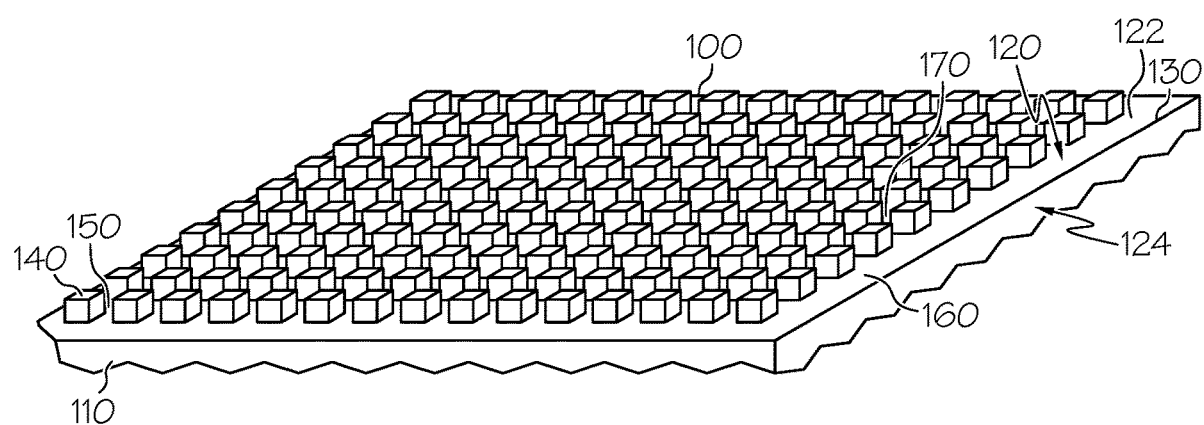
FIG. 2 is a schematic perspective view of a portion of an example spinal interbody cage including pillars.

As shown in FIG. 2, each pillar 140 that extends from the top face 120 or the bottom face 121 is integral to the bulk interbody cage 110, i.e. the bulk interbody cage 110 and the pillars 140 extending therefrom are made from the same starting material, rather than, for example, the pillars 140 being an add-on to the bulk interbody cage 110. Like the bulk interbody cage 110, the pillars 140 that extend from the top face 120 or the bottom face 121 can be porous, e.g. including pores having diameters of, e.g. 1 to 900 μm, 100 to 800 μm, or 200 to 600 μm, or the pillars 140 can be non-porous.

Similarly, each pillar 140 that extends from the top mesh structure 180 or the bottom mesh structure 181 is integral to the top mesh structure 180 or the bottom mesh structure 181, respectively, i.e. the top mesh structure 180, the bottom mesh structure 181, and the pillars 140 extending therefrom are made from the same starting material, rather than, for example, the pillars 140 being an add-on to the top mesh structure 180 and the bottom mesh structure 181.

In some examples, the top mesh structure 180 and the bottom mesh structure 181 are integral to the bulk interbody cage 110.

As shown in FIG. 4, each pillar 140 has a distal end 430, corresponding to the distal-most portion of the pillar 140 relative to the top face 120, the bottom face 121, the top mesh structure 180, or the bottom mesh structure 181 from which the pillar 140 extends. Each pillar 140 can have distal edges 432, corresponding to edges defining the distal end 430 of each pillar 140. Each pillar 140 can also have lateral edges 434, corresponding to edges of the lateral sides of each pillar 140. The distal edges 432 and/or the lateral edges 434 can be sharp, although other rounded, angular, smooth, and/or irregular edges may be used in further examples.

Figure 5A:
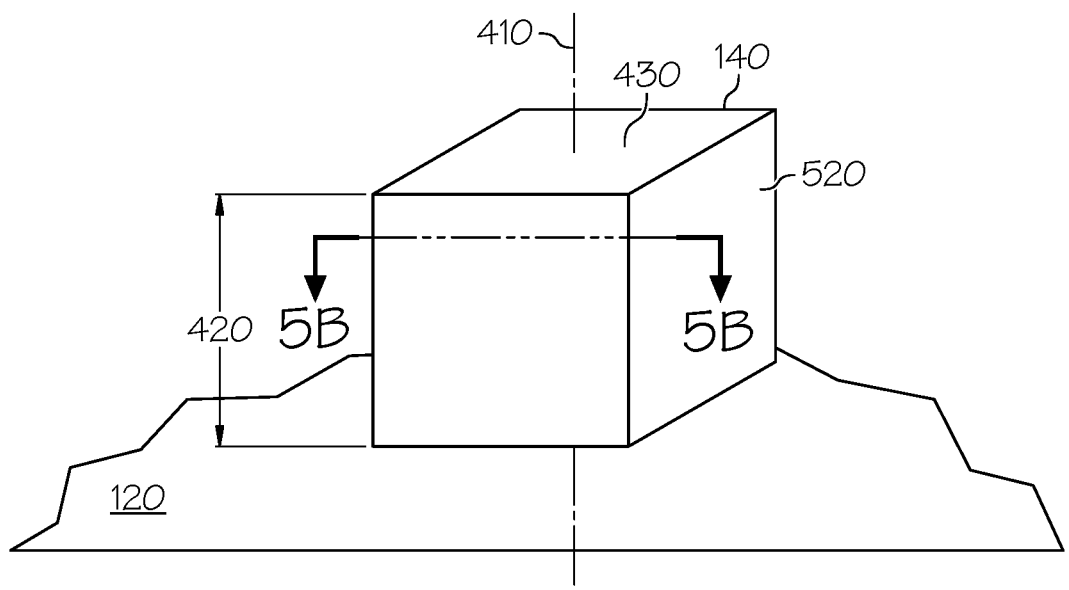
FIG. 5A is a schematic perspective view of a pillar of an example spinal interbody cage.
Figure 5B:
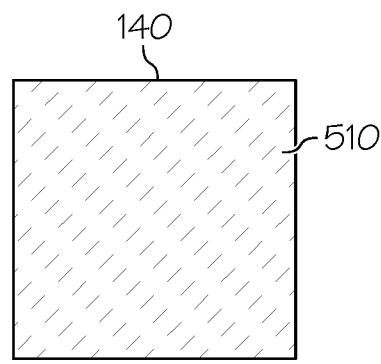
FIG. 5B is a schematic cross-sectional view of a pillar of an example spinal interbody cage.
Figure 6A:
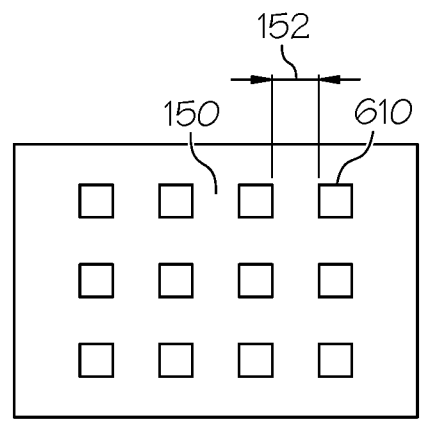
FIGS. 6A-E are schematic top plan views of portions of example spinal interbody cages including pillars in which the circumference of the transverse area of the pillars thereof have (A) a square shape, (B) a rectangular shape, (C) a herringbone shape, (D) a circular shape, and (E) an oval shape.
Figure 6B:
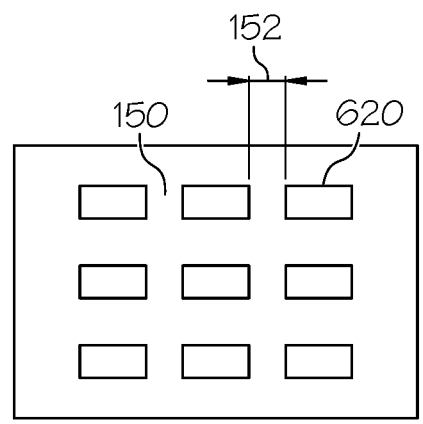
Figure 6C:
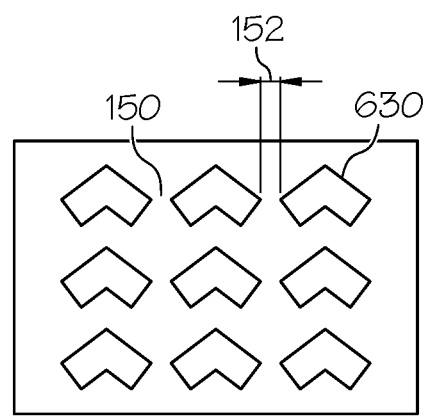
Figure 6D:
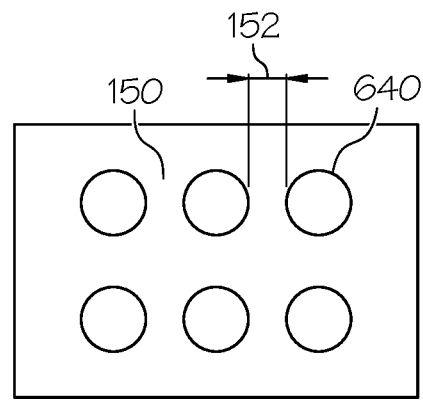
Figure 6E:
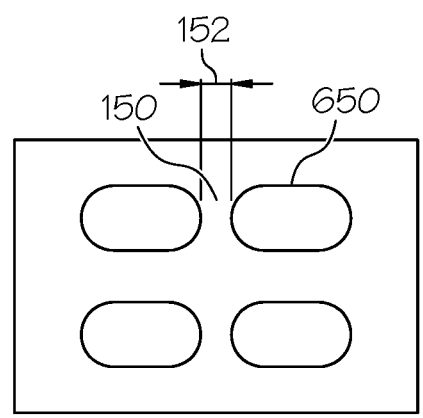

With respect to dimensions of the pillars 140, as shown in FIG. 5A and FIG. 5B, each pillar 140 has a transverse area 510, i.e. an area of a cross-section taken relative to the vertical axis 410 along which the pillar 140 extends distally from the top face 120, the bottom face 121, the top mesh structure 180, or the bottom mesh structure 181 of, for example, (i) (100 µm×100 µm) to (2,000 µm×2,000 µm), i.e. $1.0 \times 10^4$ µm² to $4.0 \times 10^6$ µm², (ii) (250 µm×250 µm) to (1,000 µm×1,000 µm), i.e. $6.3 \times 10^4$ µm² to $1.0 \times 10^6$ µm², (iii) (300 µm×300 µm) to (500 µm×500 µm), i.e. $9 \times 10^4$ µm² to $2.5 \times 10^5$ µm², (iv) (350 µm×350 µm) to (450 µm×450 µm), i.e. $1.2 \times 10^5$ µm² to $2.0 \times 10^5$ µm², or (v) (395 µm×395 µm) to (405 µm×405 µm), i.e. $1.6 \times 10^5$ µm². As shown in FIG. 4 and FIG. 5B, each pillar 140 has a pillar height 420, i.e. the height of the pillar 140 from the top face 120, the bottom face 121, the top mesh structure 180, or the bottom mesh structure 181 of the spinal interbody cage 100 to the distal end 430 of the pillar 140, of, for example, 100 to 2,500 µm, 200 to 1,000 µm, 400 to 600 µm, 450 to 550 µm, 490 to 510 µm, or 500 µm. As shown in FIG. 5A, each pillar 140 has a volume 520, i.e. product of pillar transverse area 510 and pillar height 420.

As shown in FIG. 1, with respect to the lateral spinal interbody cage 1001, with reference to FIG. 2, FIG. 5A, and FIG. 5B, in some examples the pillars 140 extending from the top face 120 or the bottom face 121 can all have identical dimensions, e.g. identical pillar transverse areas 510, pillars heights 420, and thus identical individual volumes.

Figure 18:
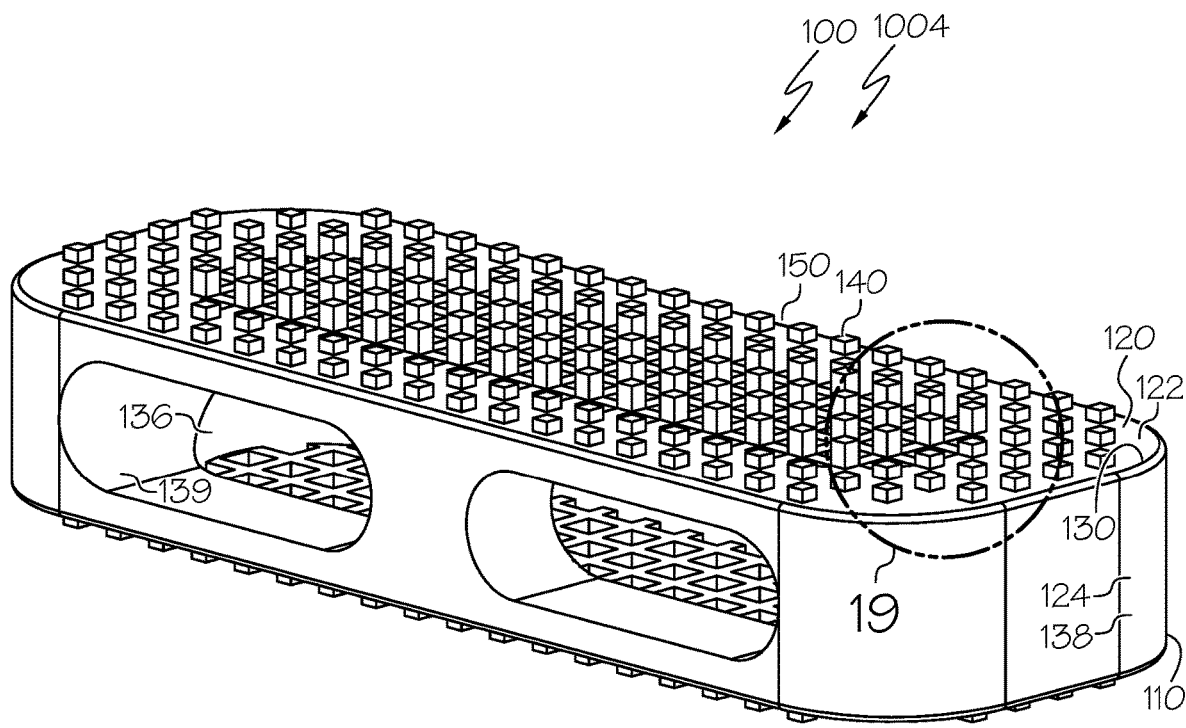
FIG. 18 is a top perspective view of an example spinal interbody cage including pillars in which the spinal interbody cage has a parallel profile and some pillars have pillar heights that are different than those of other pillars.
Figure 19:
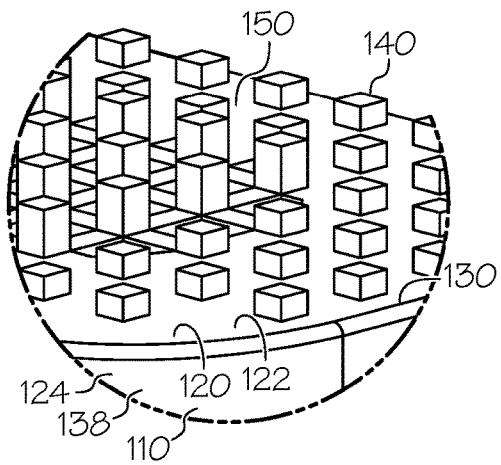
FIG. 19 is an expanded top perspective view of a portion of the spinal interbody cage of FIG. 18.
Figure 20:
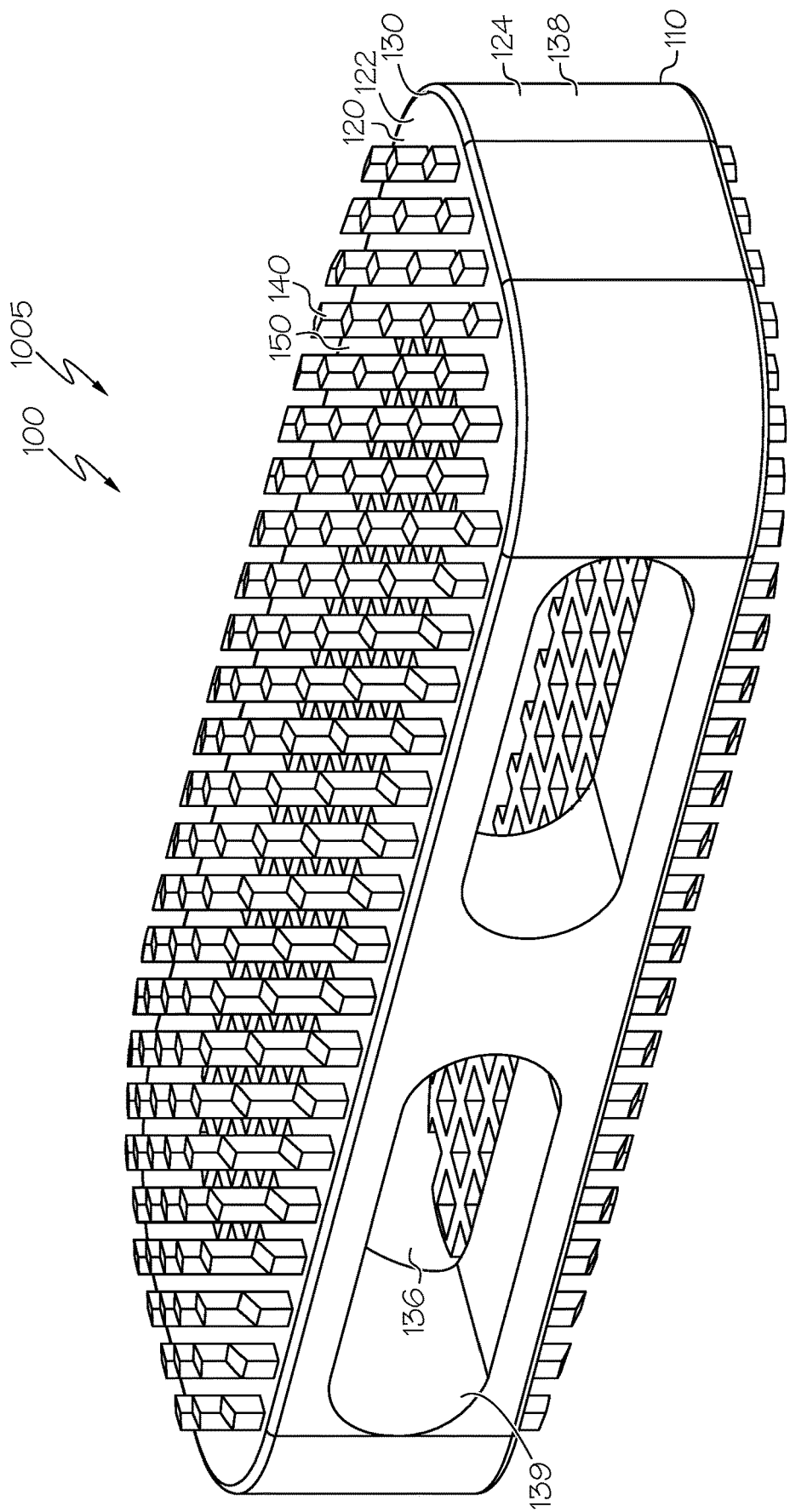
FIG. 20 is a top perspective view of an example spinal interbody cage including pillars in which the spinal interbody cage has a parallel profile and the spinal interbody cage provides an endplate profile based on the heights of the one or more pillars differing from those of the other pillars, and the spinal interbody cage having a parallel height.
Figure 21:
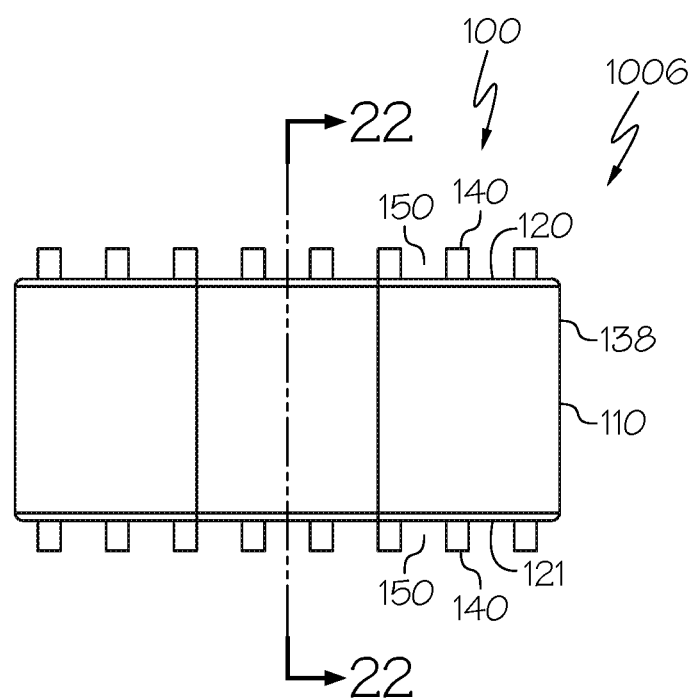
FIG. 21 is a side elevational view of an example spinal interbody cage similar to that of FIG. 1 in which the spinal interbody cage has a parallel profile and the spinal interbody cage comprises at least one interior surface comprising pillars extending therefrom, and those pillars all have identical pillars heights.

Alternatively, as shown in FIG. 18 and FIG. 20, with respect to the lateral spinal interbody cages 1004 and 1005, in some examples one or more pillars 140 can have dimensions that differ from those of other pillars 140, such that the pillar transverse areas 510 and/or pillar heights 420, and thus volumes, of the one or more pillars 140 differ from those of the other pillars 140. As shown in FIG. 20, with respect to the lateral spinal interbody cage 1005, in such cases, the spinal interbody cage 100 can provide an endplate profile based on the pillar heights 420 of the one or more pillars 140 differing from those of the other pillars 140, and the spinal interbody cage 100 can have a parallel height.

Turning to FIG. 6A to FIG. 6E, the pillars 140 can have, as seen from a top view, a square shape, a rectangular shape, a herringbone shape, a circular shape, or an oval shape, or alternatively can have other polygonal, curvilinear, or variable shapes. For example, in some embodiments all pillars 140 can have the same shape, e.g. a square shape, a rectangular shape, a herringbone shape, a circular shape, or an oval shape, as seen from a top view. Also for example, in some embodiments not all pillars 140 have the same shape as seen from a top view.

Considering now the slots 150 in more detail, the slots 150 are to be occupied by the bone of vertebral bodies and/or bone of bone graft. For example, upon implantation of the spinal interbody cage 100 between adjacent vertebral bodies, the bone can immediately occupy at least part of the space corresponding to the slots 150. This can be accomplished, for example, based on penetration of the pillars 140 of the spinal interbody cage 100 into the bone of vertebral bodies to at least some extent. Moreover, bone of vertebral bodies and/or bone of bone graft can eventually occupy part or all of the space corresponding to the slots 150 based on remodeling and/or growth of the bone over time, e.g. based on growth of bone during healing.

As shown in FIG. 2, FIG. 3, and FIG. 4, the pillars 140 define the slots 150 therebetween, i.e. the slots 150 are the spaces between the pillars 140. Accordingly, as shown in FIG. 4, the slots 150 have a slot height 440 as defined by the pillars 140, of, for example, 100 to 2,500 µm, 200 to 1,000 µm, 400 to 600 µm, 450 to 550 µm, 490 to 510 µm, or 500 µm. As shown in FIG. 6A to FIG. 6E, the slots 150 have a slot width 152 as measured along the shortest distance between adjacent pillars 140 of, for example, 100 to 2,500 µm, 150 to 1,000 µm, 175 to 450 µm, 190 to 410 µm, 190 to 210 µm, or 390 to 410 µm. The slots 150 have a volume 710 corresponding to the volume of the space between the pillars 140.

The slots 150 intersect between the pillars 140. Accordingly, the spinal interbody cage 100 includes a plurality of adjacent rows or other groupings of the pillars 140.

The spinal interbody cage 100 has a ratio of (i) the sum of the volumes 710 of the slots 150 to (ii) the sum of the volumes 520 of the pillars 140 and the volumes 710 of the slots 150, of, for example, 0.40:1 to 0.90:1, 0.51:1 to 0.90:1, 0.51:1 to 0.60:1, or 0.70:1 to 0.76:1. Without wishing to be bound by theory, it is believed that this ratio determines the approximate percentages of bone of vertebral bodies and/or bone of bone graft and spinal interbody cage 100 that will occupy the interface following implantation of the spinal interbody cage 100, e.g. that upon penetration of pillars 140 of the spinal interbody cage 100 into the bone of vertebral bodies and/or upon remodeling and growth of the bone of vertebral bodies and/or bone of bone graft following implantation, that the bone will occupy all or essentially all of the space corresponding to the slots 150 of the spinal interbody cage 100.

Figure 7:
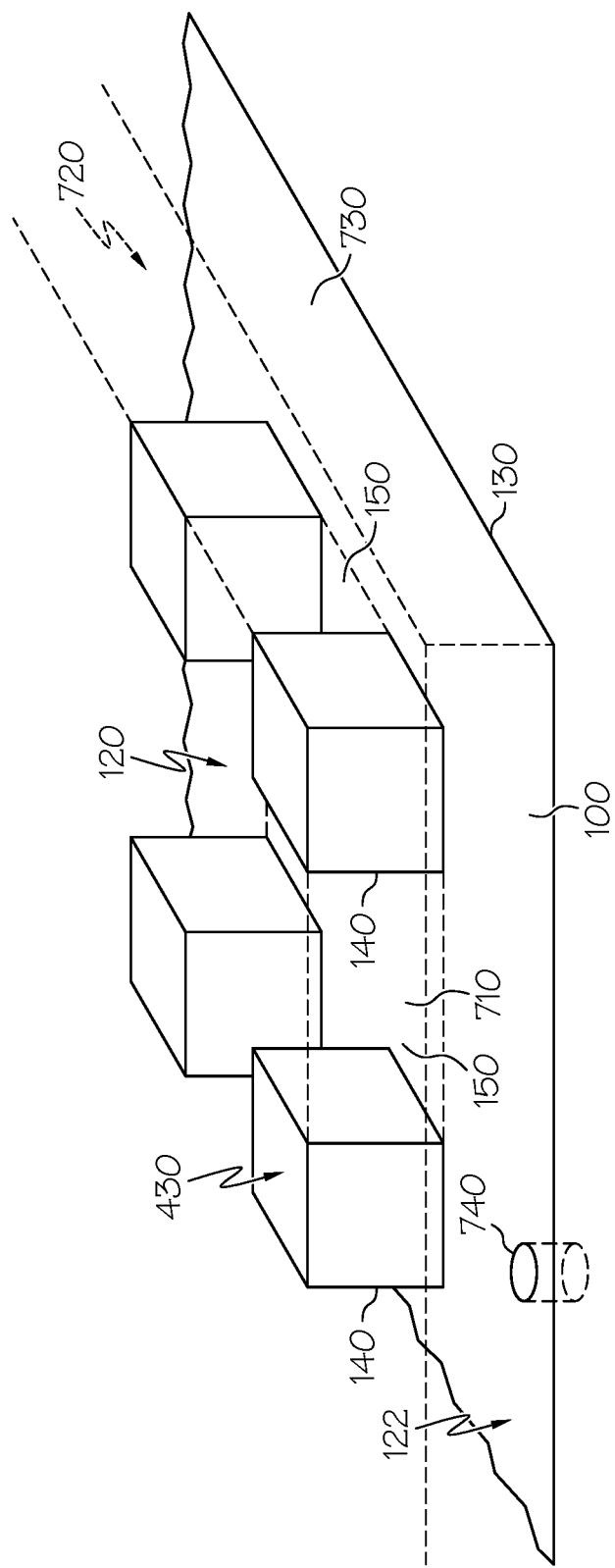
FIG. 7 is a schematic perspective view of part of a portion of an example spinal interbody cage including pillars.

More specifically, considering the top face 120 and the top mesh structure 180, and with reference to FIG. 7, the interface includes (i) the pillars 140, (ii) the slots 150 of the spinal interbody cage 100, which have a volume 710 and which, upon or following implantation, become occupied by bone of vertebral bodies and/or bone of bone graft, (iii) any additional space between the top face 120 and the top mesh structure 180 and a plane 720 defined by the distal ends 430 of the pillars 140, e.g. (a) space between the outer peripheral border 122 of the top face 120 that is not occupied by pillars 140 and the plane 720, (b) space between the inner peripheral border 126 of the top face 120 that is not occupied by pillars 140 and the plane 720, and (c) space between the top central opening 134 and/or the top mesh structure 180, though not including space within the top mesh openings 183, that is not occupied by pillars 140 and the plane 720, which has a volume 730, and which also becomes occupied by bone of vertebral bodies and/or bone of bone graft, and (iv) any pores 740 on the top face 120, the top mesh structure 180, or the pillars 140, which, depending on the size of the pores 740, may also become occupied by bone of vertebral bodies and/or bone of bone graft. Turning to the bottom face 121 and the bottom mesh structure 181, the interface also includes analogous features with respect to the bottom face 121 and the bottom mesh structure 181.

Accordingly, for example, a ratio of the sum of (i) the volumes 710 of the slots 150 to (ii) the sum of the volumes 520 of the pillars 140 and the volumes 710 of the slots 150 of 0.40:1 would, following implantation of a spinal interbody cage 100 and subsequent remodeling and growth of bone of vertebral bodies and/or bone of bone graft, wherein the spinal interbody cage 100 includes an outer edge 130 of the top face 120 and an outer edge 131 of the bottom face 121, and for which pillars 140 are located at these edges, result in an interface that includes by volume 40% bone and 60% spinal interbody cage 100, and more particularly 60% pillars 140 of the spinal interbody cage 100. Similarly, a ratio of (i) the sum of the volumes 710 of the slots 150 to (ii) the sum of the volumes 520 of the pillars 140 and the volumes 710 of the slots 150 of 0.40:1 would, following implantation of a spinal interbody cage 100 and subsequent remodeling and growth of bone of vertebral bodies and/or bone of bone graft, wherein the spinal interbody cage 100 includes an outer edge 130 of the top face 120 and an outer edge 131 of the bottom face 121, and for which no pillars 140 are located at these edges, result in an interface that includes by volume more than 40% bone and less than 60% spinal interbody cage 100, with the percentage of bone increasing, and the percentage of spinal interbody cage 100 decreasing, with increasing distance between the peripheral-most pillars 140 and slots 150 and the outer edge 130 and the outer edge 131 of the spinal interbody cage 100. By way of further examples, ratios of 0.51:1, 0.60:1, 0.70:1, 0.76:1, and 0.90:1, would result in interfaces that include, by volume, 51% bone and 49% spinal interbody cage 100, 60% bone and 40% spinal interbody cage 100, 70% bone and 30% spinal interbody cage 100, 76% bone and 24% spinal interbody cage 100, and 90% bone and 10% spinal interbody cage, respectively, for a spinal interbody cage 100 wherein the spinal interbody cage 100 includes such edges and for which pillars 140 are located at the edges. Moreover, the percentage of bone would increase, and the percentage of spinal interbody cage 100 would decrease, with increasing distance between the peripheral-most pillars 140 and slots 150 and the edges of the spinal interbody cage 100. It is further believed that by achieving an interface that is at least 40% bone, but that has a sufficient amount of the spinal interbody cage 100 to provide support and to keep the spinal interbody cage 100 from migrating, that the interface will exhibit properties similar to those of the bulk bone of vertebral bodies adjacent to the interface, e.g. high resilience to compression, rotational shear, and vertical shear.

Considering example embodiments of the spinal interbody cage 100 in more detail, in one example embodiment, the Young's modulus of the spinal interbody cage 100 is 18 to 25 GPa and the ratio of (i) the sum of the volumes 710 of the slots 150 to (ii) the sum of the volumes 520 of the pillars 140 and the volumes 710 of the slots 150 is 0.51:1 to 0.60:1. In another example embodiment, the Young's modulus of the spinal interbody cage 100 is 100 to 110 GPa and the ratio of (i) the sum of the volumes 710 of the slots 150 to (ii) the sum of the volumes 520 of the pillars 140 and the volumes 710 of the slots 150 is 0.70:1 to 0.76:1. In another example embodiment, the spinal interbody cage 100 is made of implantable-grade polyetheretherketone with filler, the transverse area 510 of each pillar 140 is (350 µm×350 µm) to (450 µm×450 µm), the pillar height 420 of each pillar 140 is 400 to 600 µm, the slot width 152 of each slot 150 is 190 to 210 µm, and the ratio of (i) the sum of the volumes 710 of the slots 150 to (ii) the sum of the volumes 520 of the pillars 140 and the volumes 710 of the slots 150 is 0.85:1 to 1.6:1. In another example embodiment, the spinal interbody cage 100 is made of implantable-grade polyetheretherketone with filler, the transverse area 510 of each pillar 140 is (395 µm×395 µm) to (405 µm×405 µm), the pillar height 420 of each pillar 140 is 490 to 510 µm, the slot width 152 of each slot 150 is 190 to 210 µm, and the ratio of (i) the sum of the volumes 710 of (ii) the slots 150 to the sum of the volumes 520 of the pillars 140 and volumes 710 of the slots 150 is 0.92:1 to 1.4:1. In another example embodiment, the spinal interbody cage 100 is made of titanium, the transverse area 510 of each pillar 140 is (350 µm×350 µm) to (450 µm×450 µm), the pillar height 420 of each pillar 140 is 400 to 600 µm, the slot width 152 of each slot 150 is 390 to 410 µm, and the ratio of (i) the sum of the volumes 710 of the slots 150 to (ii) the sum of the volumes 520 of the pillars 140 and the volumes 710 of the slots 150 is 2.2:1 to 3.7:1. In another example embodiment, the spinal interbody cage 100 is made of titanium, the transverse area 510 of each pillar 140 is (395 µm×395 µm) to (405 µm×405 µm), the pillar height 420 of each pillar 140 is 490 to 510 µm, the slot width 152 of each slot 150 is 390 to 410 µm, and the ratio of (i) the sum of the volumes 710 of the slots 150 to (ii) the sum of the volumes 520 of the pillars 140 and the volumes 710 of the slots 150 is 2.4:1 to 3.5:1.

As noted above, as shown in FIG. 1, with reference to FIG. 9 and FIG. 10, with respect to the lateral spinal interbody cage 1001, in some embodiments the spinal interbody cage 100 has a parallel profile. Also, as shown in FIG. 30, with reference to FIG. 31 and FIG. 32, with respect to the lateral spinal interbody cage 1011, in some embodiments, the spinal interbody cage 100 has a lordotic profile. Also, as shown in FIG. 33, with reference to FIG. 34 and FIG. 35, with respect to the lateral spinal interbody cage 1012, in some embodiments, the spinal interbody cage 100 has a domed profile.

In accordance with these embodiments, the pillars 140 may be understood to define a theoretical top surface of the spinal interbody cage 100, at the distal ends 430 of pillars 140 extending from the top face 120 and the top mesh structure 180, and a theoretical bottom surface of the spinal interbody cage 100, at the distal ends 430 of pillars 140 extending from the bottom face 121 and the bottom mesh structure 181, of the spinal interbody cage 100.

In this context, a spinal interbody cage 100 having a parallel profile has a theoretical top surface and a theoretical bottom surface that define top and bottom planes that are parallel with respect to each other and that have no height differences across the respective theoretical top and bottom surfaces. Of note, there may be localized variance from these parallel planes (e.g. a tapered leading edge to ease insertion of one or more tall pillars 140 that extend above the theoretical surface to provide enhanced initial fixation) but, in bulk (i.e. considering the majority of the pillars 140, and excluding pillars 140 that are outliers), the theoretical top and bottom surfaces define planes that are parallel with respect to each other.

Also in this context, a spinal interbody cage 100 having a lordotic profile has a theoretical top surface and a theoretical bottom surface that define planes that diverge with respect to each other and that have gradually increasing height differences across the respective surfaces when traversing from one end of the implant to the opposite end. Again, there may be localized variance from these diverging planes (e.g. a tapered leading edge to ease insertion of one or more tall pillars 140 that extend above the theoretical surface to provide enhanced initial fixation) but, in bulk, the theoretical top and bottom surfaces define planes that diverge with respect to each other.

Also in this context, a spinal interbody cage 100 having a domed profile has a theoretical top surface and/or a theoretical bottom surface that has an arched contour. The corresponding arch may be in a direction oriented with the length of the cage, in a direction oriented with the width of the cage, or in both directions. For example, the domed profile may be defined by a cylindrical shape in one direction or by an ovoid shape over the entire surface. The spinal interbody cage 100 may have a domed profile on top and a flat profile on bottom, or may have a domed profile on bottom and a flat profile on top, or may have domed profiles on both top and bottom. In some examples the domed surfaces may be defined on the spinal interbody cage 100 with essentially equal heights at distal and proximal ends of the spinal interbody cage 100 (a parallel profile with a domed top and/or bottom), or with heights being different at distal and proximal ends of the spinal interbody cage 100 (a lordotic profile with a domed top and/or bottom). Again, there may be localized variance from these domed profiles (e.g. a tapered leading edge to ease insertion of one or more tall pillars 140 that extend above the theoretical surface to provide enhanced initial fixation) but, in bulk, the theoretical top and/or bottom surfaces have an arched contour.

In some examples, the pillars 140 are distributed and dimensioned to provide immediate micro-subsidence following implantation in a patient, between adjacent vertebral bodies, thereby providing post-operative interdigitated fixation and stability.

As shown in FIG. 1, with respect to the lateral spinal interbody cage 1001, in some examples, the spinal interbody cage 100 includes at least one lateral exterior surface 138. Also as shown in FIG. 1, in some examples the lateral exterior surface 138 can include one or more lateral surface openings 139. As shown in FIG. 29, with respect to the lateral spinal interbody cage 1010, also in some examples the lateral exterior surface 138 can include pillars 140 extending from the lateral exterior surface 138.

Figure 11:
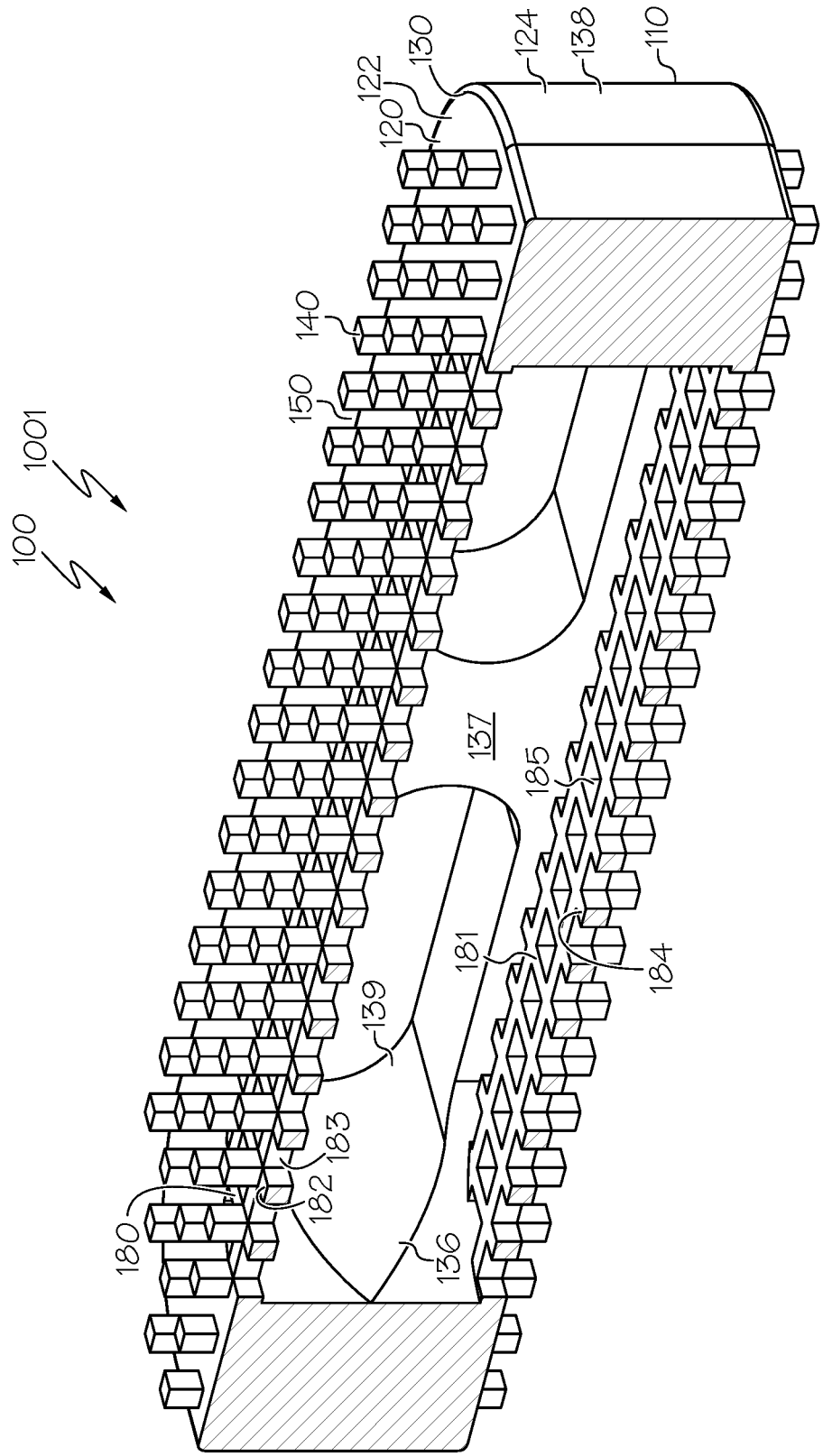
FIG. 11 is a sectional view of the spinal interbody cage of FIG. 10.
Figure 22:
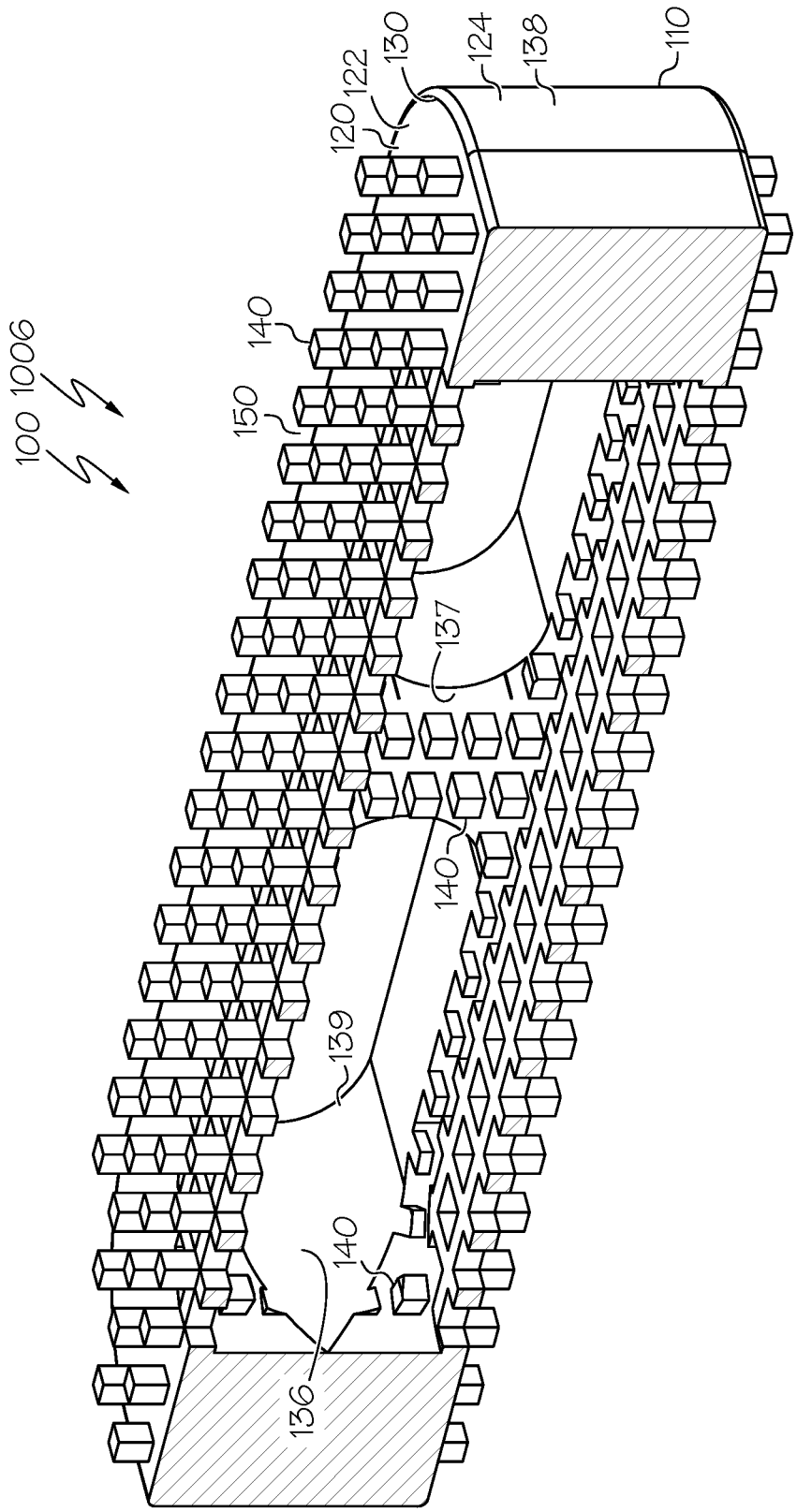
FIG. 22 is a sectional view of the spinal interbody cage of FIG. 21.
Figure 23:
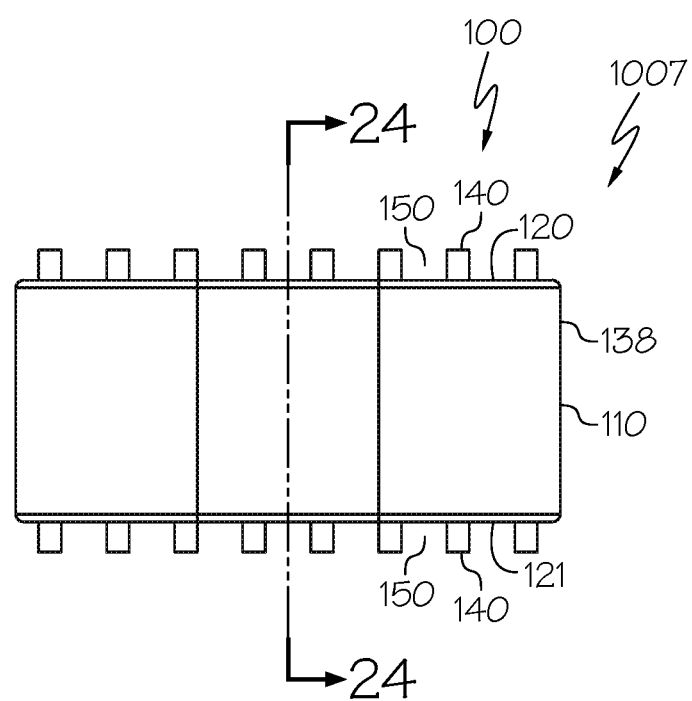
FIG. 23 is a side elevational view of an example spinal interbody cage similar to that of FIG. 1 in which the spinal interbody cage has a parallel profile and the spinal interbody cage comprises at least one interior surface comprising pillars extending therefrom, and some of those pillars have pillar heights that are different than the pillar heights of others of those pillars.
Figure 24:
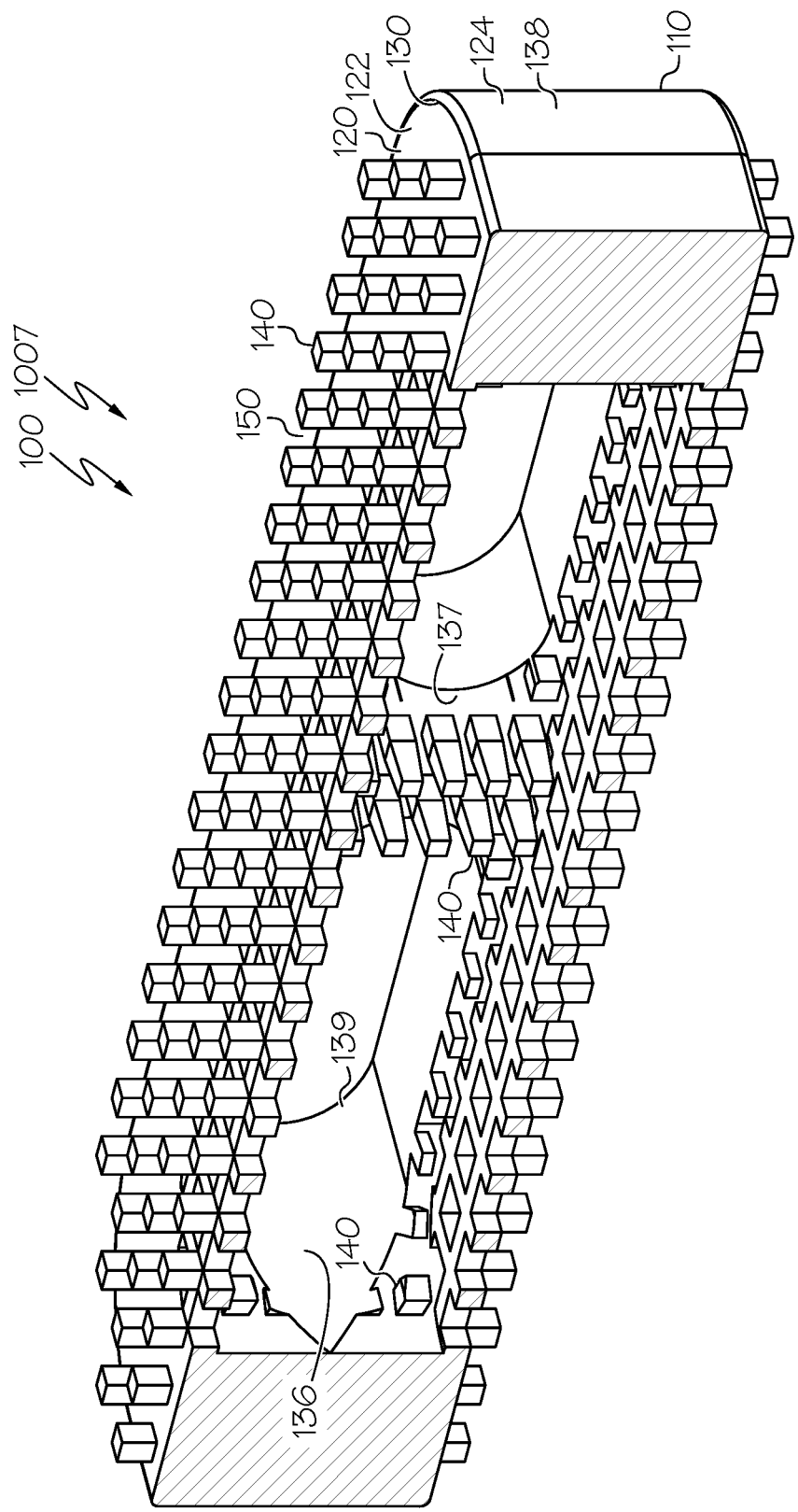
FIG. 24 is a sectional view of the spinal interbody cage of FIG. 23.
Figure 25:
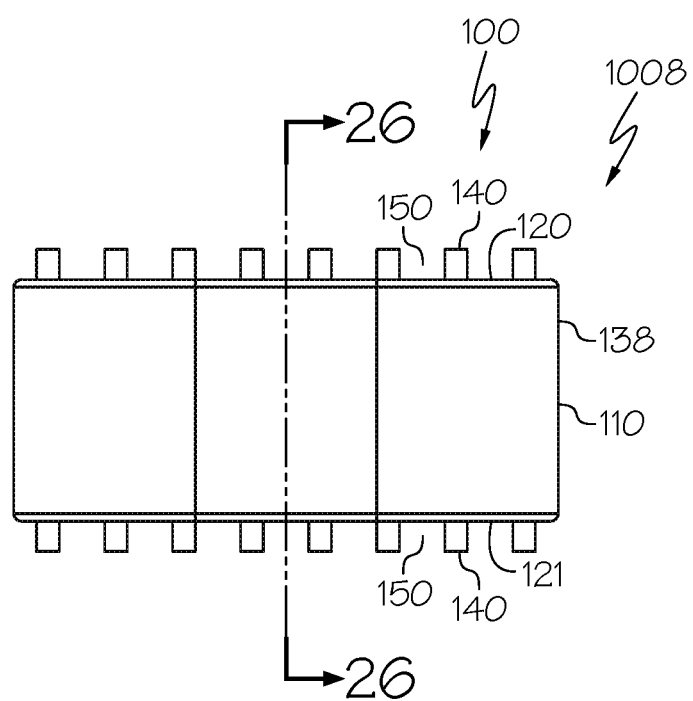
FIG. 25 is a side elevational view of another example spinal interbody cage similar to that of FIG. 1 in which the spinal interbody cage has a parallel profile and the spinal interbody cage comprises at least one interior surface comprising pillars extending therefrom, and those pillars all have identical pillars heights.
Figure 26:
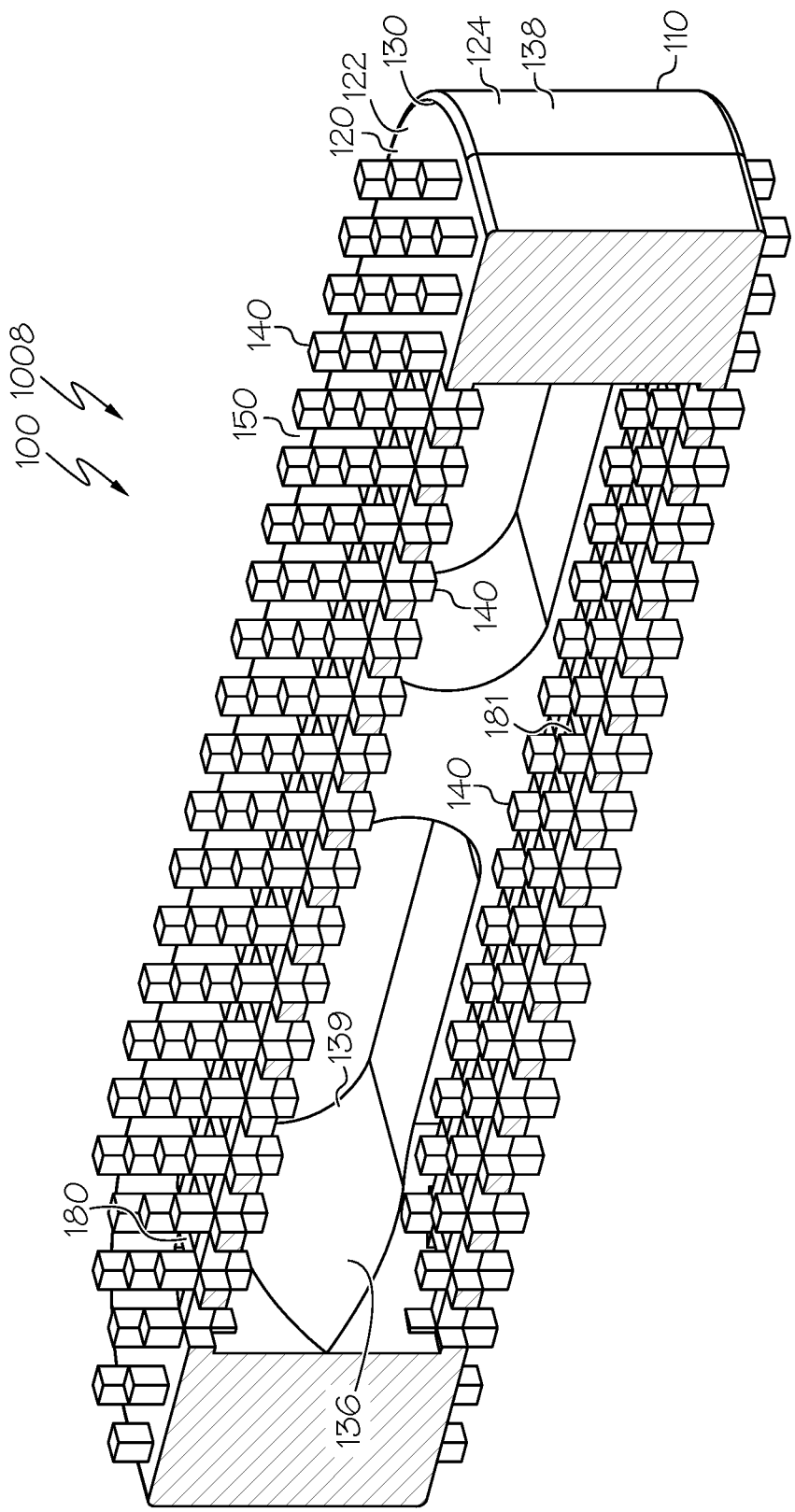
FIG. 26 is a sectional view of the spinal interbody cage of FIG. 25.
Figure 27:
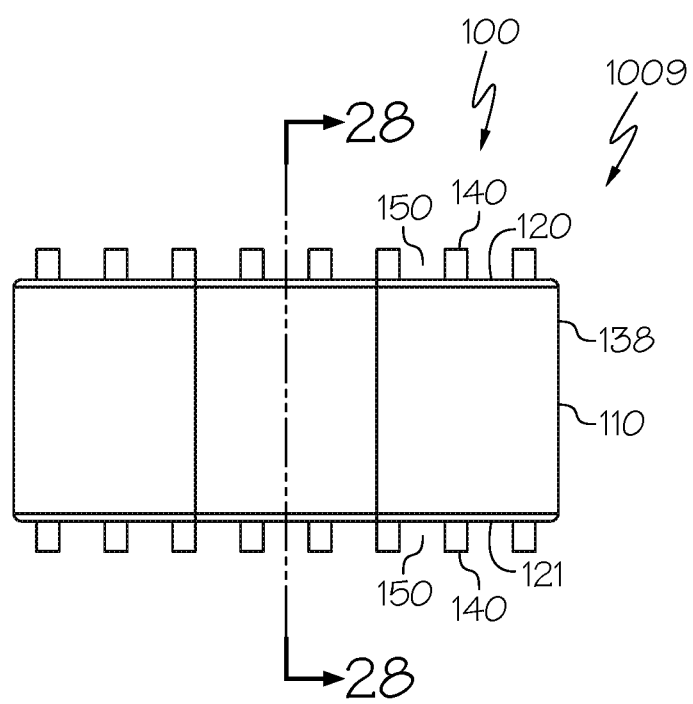
FIG. 27 is a side elevational view of another example spinal interbody cage similar to that of FIG. 1 in which the spinal interbody cage has a parallel profile and the spinal interbody cage comprises at least one interior surface comprising pillars extending therefrom, and some of those pillars have pillar heights that are different than the pillar heights of others of those pillars.

Also as shown in FIG. 11, with reference to FIG. 10, with respect to the lateral spinal interbody cage 1001, in some examples, the spinal interbody cage 100 includes at least one interior surface 137. As shown in FIG. 22, FIG. 24, FIG. 26, and FIG. 28, with reference to FIG. 21, FIG. 23, FIG. 25, and FIG. 27, respectively, with respect to the lateral spinal interbody cages 1006, 1007, 1008, and 1009, respectively, in some examples the interior surface 137 can include pillars 140 extending from the interior surface 137. As shown in FIG. 22 and FIG. 24, with respect to the lateral spinal interbody cages 1006 and 1007, respectively, in some of these examples the interior surface 137 from which the pillars 140 may extend can be an interior surface 137 of the bulk interbody cage 110. As shown in FIG. 26 and FIG. 28, with respect to the lateral spinal interbody cages 1008 and 1009, respectively, in some of these examples the interior surface 137 from which the pillars 140 may extend can be an interior surface 137 of the top mesh structure 180 and/or the bottom mesh structure 181. Pillars 140 extending from the interior surface 137 may promote bridging of bone between adjacent vertebral bodies through the central cavity 136 of the spinal interbody cage 100.

As shown in FIG. 22 and FIG. 26, with respect to the lateral spinal interbody cages 1006 and 1008, respectively, similarly as for pillars 140 extending distally from the top face 120, the bottom face 121, the top mesh structure 180, and the bottom mesh structure 181 as discussed above, in some examples a plurality of the pillars 140 extending from the interior surface 137 can have identical dimensions, e.g. identical pillar transverse areas 510, pillars heights 420, and thus identical individual volumes.

Also, as shown in FIG. 24 and FIG. 28, with respect to the lateral spinal interbody cages 1007 and 1009, respectively, in some examples one or more pillars 140 extending from the interior surface 137 can have dimensions that differ from those of other pillars 140, such that the pillar transverse areas 510 and/or pillar heights 420, and thus volumes, of the one or more pillars 140 differ from those of the other pillars 140. Pillars 140 extending from the interior surface 137 and having different heights may promote better holding of bone graft within the central cavity 136 of the spinal interbody cage 100.

Also disclosed are spinal interbody cages like the spinal interbody cage 100 as disclosed above and as follows, but including pillars 140 extending from the top face 120 and/or the top mesh structure 180, but not from the bottom face 121 and/or the bottom mesh structure 181, or including pillars 140 extending from the bottom face 121 and/or the bottom mesh structure 181, but not from the top face 120 and/or the top mesh structure 180, or not including pillars 140 extending from the top face 120 and/or the top mesh structure 180 or the bottom face 121 and/or the bottom mesh structure 181. Further disclosed are such spinal interbody cages also including pillars extending from at least one lateral exterior surface 138, or pillars extending from at least one interior surface 137, or both.

In some examples, the pillars 140 include, at their distal ends 430, a roughened surface. The roughened surface may promote resistance of the pillars 140 to expulsion from bone of the adjacent vertebral bodies.

In some examples, the transverse area 510 of one or more of the pillars 140 increases distally. For example, as shown in FIG. 14, with reference to FIG. 15, with respect to the lateral spinal interbody cage 1002, in some embodiments the transverse area 510 of at least 50%, at least 60%, at least 70%, at least 80%, at least 90%, at least 95%, or all of the pillars 140 increases distally. In accordance with these embodiments, the pillars 140 can be inversely tapered distally. This may promote gripping of the pillars 140 normal to the interface resulting from the implantation.

In some examples, the transverse area 510 of one or more of the pillars 140 does not decrease distally. For example, as shown in FIG. 1, with respect to the lateral spinal interbody cage 1001, in some embodiments the transverse area 510 of at least 50%, at least 60%, at least 70%, at least 80%, at least 90%, at least 95%, or all of the pillars 140 does not decrease distally. Also in some examples, the transverse area 510 of one or more of the pillars 140 can be substantially constant along the vertical axis 410 along which the one or more pillars 140 extend distally. For example, also as shown in FIG. 1, with respect to the lateral spinal interbody cage 1001, in some embodiments the transverse area 510 of at least 50%, at least 60%, at least 70%, at least 80%, at least 90%, at least 95%, or all of the pillars 140 is substantially constant along the vertical axis 410 along which the one or more pillars 140 extend distally. In accordance with these embodiments, the distal end 430 of the one or more pillars 140 can have a distal end area, defined by the distal edges 432 of the one or more pillars 140, that is substantially equal to the transverse area 510 of the one or more pillars 140. This also may promote gripping of the pillars 140 normal to the interface resulting from the implantation.

The spinal interbody cage 100 can be made from the materials noted above by methods such as laser cutting, injection molding, 3D printing, and other fabrication methods that are known in the art.

The spinal interbody cage 100 can be implanted between adjacent vertebral bodies, e.g. adjacent vertebral bodies from among C2-T1 vertebrae, adjacent vertebral bodies from among T1-T12 vertebrae, adjacent vertebral bodies of L4-L5 vertebra, and adjacent vertebral bodies of L5-S1 vertebrae, among others, by standard methods for implantation of spinal interbody cages.

In some embodiments, the implanting can be done such that bone graft is included within the spinal interbody cage 100, e.g. within the central cavity 136 of the spinal interbody cage 100. The bone graft can be included with the spinal interbody cage 100, for example, by placement through one or more lateral surface openings 139 in a lateral exterior surface 138, as discussed above. In accordance with these embodiments, the bone of bone graft can remodel and grow to fill in part or all space between the spinal interbody cage 100 and the adjacent vertebral bodies, including through the top mesh openings 183 and the bottom mesh openings 185, and into the slots 150 of the spinal interbody cage 100 following implantation.

Also in some embodiments, additional hard tissue can be added to the top face 120, the bottom face 121, the top mesh structure 180, the bottom mesh structure 181, and/or the pillars 140 of the spinal interbody cage 100 prior to implanting. For example, shavings of hard-tissue of a patient, generated during preparation work including sawing or drilling of hard tissue of the patient, can be added. This may promote growth of tissue into the slots 150, and through the top mesh openings 183 and the bottom mesh openings 185, of the spinal interbody cage 100 following implantation.

Also in some embodiments, additional compositions can be added to the top face 120, the bottom face 121, the top mesh structure 180, the bottom mesh structure 181, and/or the pillars 140 of the spinal interbody cage 100 prior to implanting. Such compositions include, for example, blood, one or more antibiotics, one or more osteogenic compounds, bone marrow aspirate, and/or surface chemistry for inducing early bone ingrowth. For example, the top face 120, the bottom face 121, the top mesh structure 180, the bottom mesh structure 181, and/or the pillars 140 can be coated with one or more such compositions, with the pillars 140 retaining the compositions during implantation. This also may promote growth of tissue into the slots 150, and through the top mesh openings 183 and the bottom mesh openings 185, of the spinal interbody cage 100 following implantation.

Also in some embodiments, a microtexture can be applied to the top face 120, the bottom face 121, the top mesh structure 180, the bottom mesh structure 181, and/or the pillars 140 of the spinal interbody cage 100 prior to implanting. The microtexture can correspond, for example, to a micro-topography. The microtexture can be applied, for example, by laser. The spinal interbody cage 100 to which the microtexture is applied can be one made from any one or more of the materials noted above, including, for example, implantable-grade polyaryletherketone that is essentially unfilled, titanium, or stainless steel. The spinal interbody cage 100 to which the microtexture is applied also can be one made from any one or more of the hard tissues noted above, including, for example, human hard tissue, human bone, or cadaver bone, among others. This also may promote growth of tissue into the slots 150, and through the top mesh openings 183 and the bottom mesh openings 185, of the spinal interbody cage 100 following implantation.

Also, in some embodiments, the implanting can also be done without use of adhesives, e.g. cement or grout. Also, in some embodiments, the implanting can be done without use of screws.

It will be apparent to those skilled in the art that various modifications and variations can be made without departing from the spirit and scope of the claimed invention.

What is claimed is:

1. A spinal interbody cage comprising:
   (a) a bulk interbody cage;
   (b) a top face being a top exterior surface of the bulk interbody cage and having a top central opening;
   (c) a bottom face being a bottom exterior surface of the bulk interbody cage and having a bottom central opening;
   (d) a top mesh structure extending from the bulk interbody cage across the top central opening, comprising top mesh links, and having top mesh openings between the top mesh links, each top mesh link having a width of 100 to 2,000 µm, and each top mesh opening having a mesh opening area of $(100 \times 100)$ to $(2,500 \times 2,500)$ µm$^2$;
   (e) a bottom mesh structure extending from the bulk interbody cage across the bottom central opening, comprising bottom mesh links, and having bottom mesh openings between the bottom mesh links, each bottom mesh link having a width of 100 to 2,000 µm, and each bottom mesh opening having a mesh opening area of $(100 \times 100)$ to $(2,500 \times 2,500)$ µm$^2$;
   (f) pillars for contacting vertebral bodies, the pillars being distributed on the top face, the bottom face, the top mesh structure, and the bottom mesh structure, and extending distally therefrom, across areas of at least 25 mm$^2$ of each of the top face, the bottom face, the top mesh structure, and the bottom mesh structure, each pillar that extends from the top face or the bottom face being integral to the bulk interbody cage, each pillar that extends from the top mesh structure or the bottom mesh structure being integral to the top mesh structure or the bottom mesh structure, respectively, and each pillar having a distal end, a transverse area of $(100 \times 100)$ to $(2,000 \times 2,000)$ µm$^2$, and a height of 100 to 2,500 µm; and
   (g) slots to be occupied by bone of the vertebral bodies and/or by bone of a bone graft, the slots being defined by the pillars, the slots intersecting between the pillars, and each slot having a width of 100 to 2,500 µm as measured along the shortest distance between adjacent pillars; wherein:
   the spinal interbody cage has a Young's modulus of elasticity of at least 3 GPa, and has a ratio of (i) the sum of the volumes of the slots to (ii) the sum of the volumes of the pillars and the volumes of the slots of 0.40:1 to 0.90:1.

2. The spinal interbody cage of claim 1, wherein the spinal interbody cage is made of one or more materials selected from implantable-grade polyaryletherketone that is essentially unfilled, implantable-grade polyetheretherketone, implantable-grade polyetherketoneketone, titanium, stainless steel, cobalt-chromium alloy, titanium alloy, Ti-6Al-4V titanium alloy, Ti-6Al-7Nb titanium alloy, ceramic material, silicon nitride (Si3N4), implantable-grade composite material, implantable-grade polyaryletherketone with filler, implantable-grade polyetheretherketone with filler, implantable-grade polyetheretherketone with carbon fiber, or implantable-grade polyetheretherketone with hydroxyapatite.

3. The spinal interbody cage of claim 1, wherein the spinal interbody cage has a parallel profile.

4. The spinal interbody cage of claim 1, wherein the spinal interbody cage has a lordotic profile.

5. The spinal interbody cage of claim 1, wherein the spinal interbody cage has a domed profile.

6. The spinal interbody cage of claim 1, wherein a plurality of the pillars are perpendicular to the top face, a plurality of the pillars are perpendicular to the bottom face, a plurality of the pillars are perpendicular to the top mesh structure, and a plurality of the pillars are perpendicular to the bottom mesh structure.

7. The spinal interbody cage of claim 1, wherein each top mesh link and bottom mesh link has a width of 250 to 1,000 µm.

8. The spinal interbody cage of claim 1, wherein each top mesh opening and bottom mesh opening has a mesh opening area of $(150 \times 150)$ to $(1,000 \times 1,000)$ µm$^2$.

9. The spinal interbody cage of claim 1, wherein the transverse area of each pillar is $(250 \times 250) \mu m^2$ to $(1,000 \times 1,000) \mu m^2$.

10. The spinal interbody cage of claim 1, wherein the height of each pillar is 300 to 1,000 μm.

11. The spinal interbody cage of claim 1, wherein the width of each slot is 150 to 1,000 μm.

12. The spinal interbody cage of claim 1, wherein the bulk interbody cage is non-porous.

13. The spinal interbody cage of claim 1, wherein:
   one or more pillars have dimensions that differ from those of other pillars, such that the transverse areas and/or heights, and thus volumes, of the one or more pillars differ from those of the other pillars; and
   the spinal interbody cage provides an endplate profile based on the heights of the one or more pillars differing from those of the other pillars, and the spinal interbody cage having a parallel height.

14. The spinal interbody cage of claim 1, wherein the pillars are distributed and dimensioned to provide immediate micro-subsidence following implantation in a patient, between adjacent vertebral bodies, thereby providing post-operative interdigitated fixation and stability.

15. The spinal interbody cage of claim 1, wherein the spinal interbody cage comprises at least one lateral exterior surface.

16. The spinal interbody cage of claim 15, wherein the at least one lateral exterior surface includes one or more lateral surface openings.

17. The spinal interbody cage of claim 15, wherein the at least one lateral exterior surface comprises pillars extending from the at least one lateral exterior surface.

18. The spinal interbody cage of claim 1, wherein the spinal interbody cage comprises at least one interior surface comprising pillars extending from the least one interior surface.

19. The spinal interbody cage of claim 1, wherein the top mesh structure and the bottom mesh structure are integral to the bulk interbody cage.

20. The spinal interbody cage of claim 1, wherein the spinal interbody cage is selected from the group consisting of an anterior lumbar interbody fusion (ALIF) spinal interbody cage, a posterior lumbar interbody fusion (PLIF) spinal interbody cage, a lateral spinal interbody cage, a direct lateral interbody fusion (DLIF) spinal interbody cage, a transforaminal lumbar interbody fusion (TLIF) spinal interbody cage, an extreme lateral interbody fusion (XLIF) spinal interbody cage, and a cervical spinal interbody cage.

* * * * *

UNITED STATES PATENT AND TRADEMARK OFFICE
CERTIFICATE OF CORRECTION

| | |
|---|---|
| PATENT NO. | : 11,278,427 B2 |
| APPLICATION NO. | : 17/046358 |
| DATED | : March 22, 2022 |
| INVENTOR(S) | : George J. Picha et al. |

It is certified that error appears in the above-identified patent and that said Letters Patent is hereby corrected as shown below:

On the Title Page

Item (73), Assignee:
"GARY A. ZICK, TRUSTEE OF THE EVEREST TRUST UTA APRIL 20, 2017"
Should read:
-- GARY A. ZWICK, TRUSTEE OF THE EVEREST TRUST UTA APRIL 20, 2017 --

Signed and Sealed this
Eleventh Day of April, 2023

Katherine Kelly Vidal
*Director of the United States Patent and Trademark Office*